(12) United States Patent
Ganey et al.

(10) Patent No.: US 12,419,991 B2
(45) Date of Patent: *Sep. 23, 2025

(54) BIOENERGETIC BONE

(71) Applicant: Vivex Biologics Group, Inc., Atlanta, GA (US)

(72) Inventors: Timothy Ganey, Tampa, FL (US); Wendy W. Weston, Miami, FL (US); Miguel Quevedo, Miami, FL (US); Stuart Oglesby, Miami, FL (US); Tracy Scott Anderson, Atlanta, GA (US)

(73) Assignee: Vivex Biologics Group, Inc., Atlanta, GA (US)

(*) Notice: Subject to any disclaimer, the term of this patent is extended or adjusted under 35 U.S.C. 154(b) by 231 days.

This patent is subject to a terminal disclaimer.

(21) Appl. No.: 17/827,934

(22) Filed: May 30, 2022

(65) Prior Publication Data
US 2022/0288274 A1    Sep. 15, 2022

Related U.S. Application Data

(62) Division of application No. 15/818,147, filed on Nov. 20, 2017, now Pat. No. 11,471,559.

(51) Int. Cl.
A61L 27/36    (2006.01)
A61K 35/28    (2015.01)
A61K 35/32    (2015.01)

(52) U.S. Cl.
CPC .......... *A61L 27/3608* (2013.01); *A61K 35/28* (2013.01); *A61K 35/32* (2013.01); *A61L 27/3604* (2013.01); *A61L 27/365* (2013.01); *A61L 27/3687* (2013.01); *A61L 27/3691* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 5,837,539 | A | * | 11/1998 | Caplan ............. C12N 5/0663 530/389.1 |
| 2002/0132012 | A1 | * | 9/2002 | Scarborough ....... A61L 27/3608 424/549 |
| 2004/0097612 | A1 | | 5/2004 | Rosenberg et al. |
| 2005/0013872 | A1 | * | 1/2005 | Freyman ............. A61K 35/28 514/9.2 |
| 2010/0112032 | A1 | | 5/2010 | Guelcher et al. |
| 2012/0053692 | A1 | * | 3/2012 | Voor .................. A61L 24/001 206/568 |
| 2014/0065240 | A1 | | 3/2014 | Mitsialis et al. |

FOREIGN PATENT DOCUMENTS

WO    2014159662    10/2014

OTHER PUBLICATIONS

Brockbank et al., Chapter 8: Tissue Preservation, Advances in Biopreservation, Jun. 2006 (Year: 2006).*
Schenke-Layland et al., Ann. Thorac Surg, 2006 (Year: 2006).*
Thibault et al Adv Healthc Mater., 2013 (Year: 2013).*
Thesaurus.com/can be, retrieved from the internet (Jun. 24, 2021): https://www.thesaurus.com/browse/can%20be (Year: 2021).
Al-Nedawi et al., Cell Cycle (2009), vol. 8, Issue 13, pp. 2014-2018 (Year: 2009).
Camussi et al., Kidney International (2010), vol. 78, pp. 838-848 (Year: 2010).
Mathivanan et al.Journal of Proteomics, vol. 73 (2010), pp. 1907-1920 (Year: 2010).
Matsumura et al., Cell Transplantation, vol. 19, pp. 691-699, 2010 (Year: 2010).
Matsumura et al., Journal of Biomaterials Science, Polymer Edition, 2013 (Year: 2013).
Weston et al., BioDrugs (2019) 33: 137-158.
Williams et al., Circulation Research, 2011; 109: 907-922.

* cited by examiner

*Primary Examiner* — Evelyn Y Pyla
(74) *Attorney, Agent, or Firm* — Kilpatrick Townsend & Townsend LLP

(57) ABSTRACT

A biological composition has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts. The mixture is compatible with biologic function.

12 Claims, 28 Drawing Sheets

| Induced current density (mA/m²) | |
|---|---|
| <1 | Endogenous |
| 1-10 | Minor |
| 10-100 | Beneficial |
| 100-1000 | Beneficial |
| >1000 | Hazardous |

PEF

NTA

BIOENERGETIC BONE

RELATED APPLICATIONS

This application is a division of U.S. application Ser. No. 15/818,147 filed on Nov. 20, 2017 entitled, "Bioenergetic Bone".

TECHNICAL FIELD

This invention relates to a bioenergetic bone matrix. More specifically, a bone matrix derived from human cadaveric cortical bone that is imbued with biologic potential gained from specified mechanical, electrical, and magnetic transfers of energy to the material defined by optimized processing and a method of manufacture and use of said matrix.

BACKGROUND OF THE INVENTION

In the area of tissue regeneration or repair, the use of stem cell therapy has been widely touted.

Often, these inventions describe isolating the stem cells, purifying and culturally expanding mesenchymal stem cells. In U.S. Pat. No. 5,837,539, entitled "Monoclonal Antibodies For Human Mesenchymal Stem Cells", Arnold Caplan et al. reported that the cells are preferably culturally expanded, but suggest it is possible to use the stem cells without culture expansion. Caplan also describes a way to isolate stem cells.

A major technological hurdle to producing a safe allogeneic composition with viable cells has been the need to approach a fraction of risk approaching zero by removing all antigenic properties that lead to inflammation factors in a separation to yield only a certain stromal cell type, with variations in composition responsive to wound conditions and replacement in ability to modulate repair. This has proven both difficult and degrading the quantity of viable cells that can be effectively harvested.

The present invention has yielded a biological composition that is safe and achieves excellent biologic function and does so in a method that allows the resultant mixture to be recovered from bone marrow wherein the mixture unexpectedly exhibits evidence of viability independent of mesenchymal cells in the dose and sustains a legacy or memory of the lineages from where the acellular biological composition came which retain the ability to support the emergence of new tissue forms including bone and other tissues.

The manufacturing of an aseptic Bioenergetic Bone Matrix derived from human cadaveric cortical bone that is imbued with biologic potential gained from specified mechanical, electrical, and magnetic transfers of energy to the material defined by optimized processing. Cortical bone is obtained from male donors or female donors. Full body cadaver donors with no joint replacements are preferred.

Accentuation of osteoinductivity, osteoconductivity, acellular packaging components, vascular induction, cell adhesion, directed morphogenesis and lateral transfer of genetic information can occur as a result of non-invasive treatment of bone material before downstream processing creating a composition that is biologically energized hereinafter called bioenergetic.

Treatment for accentuation of bioenergetics may be mechanical, atmospheric or rely on transient adjustment to membrane charge. Examples of tissue response to pressure waves, electric fields, magnetic fields, pressure variations, and ion streaming induction with pH are known in the literature. In the present invention, bioenergetics are attuned to energy transfer options that result in liposomal exchange, clathrin-based exosome expulsion, and gene tuning to modulating specific protein translation. The methods which promote these effects are PEMF (Pulsed Electro-Magnetic Fields), shockwave, negative pressure, tuned chirality, pH-induced shock and variable, impermanent membrane coating.

The demineralization process of bone tissue exposes morphogenetic proteins and other intrinsic growth factors that precipitate the osteoinductive signals that promote new bone formation. Long term integration of therapeutic effect is intended to be used in regenerative applications that offer clinical solutions for osseous defects and bone voids. Moreover, the mechanisms envisioned to extend optimized conditions of the bioenergized material will sustain and subsidize sufficient stimuli to provide metabolic support and integrated grafting of host and donor tissues. In one embodiment of the present invention, at room temperature with appropriate fluid added, Bioenergetic Bone Matrix can be moldable, ideal for bone deficit repair.

The Bioenergetic Bone Matrix product is entirely derived from aseptic allograft cortical and cancellous bone. To date, technology that transfers energy to material to alter cellular membrane activity has not been developed. Concepts and contexts envisioned in material optimization use scaffold allograft material as a sump for biologically viable components that are energetically stimulated in situ while viability remains.

The cortical bone is aseptically cleaned, cut and ground or shaved in order to obtain cortical bone particulates or shavings, respectively. In the final product, defined compositions of the cortical bone will be demineralized. The cancellous bone is cleaned, cut and crushed. Bioenergetic Bone Matrix is prepared by mixing mineralized shavings, particulate or powder, demineralized cortical shavings, particulate or powder, and crushed cancellous bone. Final Bioenergetic Bone Matrix particulate are distributed into jars and packaged. The material can be stored at room temperature to −80 C, depending on the type of product, until distribution to the end user.

These and other benefits of the present invention and the method of preparing it are described hereinafter.

SUMMARY OF THE INVENTION

A biological composition has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts. The mixture is compatible with biologic function, both in presence and absence of specific empiric composition.

The mixture of mechanically selected material derived from bone marrow. The biological composition preferably has bone particles. The bone particles can be added to the mixture derived from bone marrow. The bone particles include a mixture of cortical bone particles and cancellous bone particles.

The combination of non-whole cell components with a select number of non-whole cell fractions sustains pluripotency in the cells. In a preferred embodiment, the biological composition is predisposed to demonstrate or support elaboration of active volume or spatial geometry consistent in morphology with that of endogenous bone. The biological composition extends regenerative resonance that compliments or mimics tissue complexity. The mixture is treated in a protectant or cryoprotectant prior to preservation or cryopreservation or freeze drying. The composition can be maintained at ambient temperature prior to freeze drying. The protectant or cryoprotectant creates a physical or electrical or chemical gradient or combination thereof for tissue regeneration. The gradient can have a physical characteristic of modulus or topography, such as charge density, field shape or cryo or chemo toxic tendencies. The gradient can have a chemical characteristic of spatially changing compositions of density or species of functional molecules, wherein the molecules can offer a fixed catalytic function as a co-factor. Also, the gradient can have an electrical characteristic of charge based or pH based or electron affinities that confer metastability in biologic potential.

The bone marrow mixture which is derived from a cadaver has separation-enhanced non-whole cell fractions vitality including one or more of the following: separating the fractions from cells heightens their vitality, reversing "arrest" of donors, responsive molecular coupling, matrix quest in neutralizing inflammation or satience by balancing stimulus for repair. The protectant or cryoprotectant is a polyampholyte. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C. The protection may also be achieved by non-cryogenic means.

The biological composition's non-whole cellular component also can include organelle fragments and the active and inactive components of biological activity which can also include extants of the human metabiome.

A method of making a biological composition of the present invention has the steps of: collecting, recovering and processing bone marrow from a cadaver donor; mechanically separating the cellular or non-cellular components or a combination thereof of bone marrow from cadaverous bone; concentrating by centrifugation and filtering; separation by density gradient centrifugation; collecting non-cellular fractions or non-cellular components or a combination thereof of predetermined density; washing the non-whole cellular fractions or non-cellular components or a combination thereof to create the mixture; quantifying concentrations of non-cellular fractions components at a non-zero entity; suspending to a predetermined concentration in a polyampholyte cryoprotectant; freezing the mixture at a predetermined controlled rate; and packaging a bone blend having particles in the size range of 100 to 300 μm of demineralized cortical bone, mineralized cortical bone and mineralized cancellous bone either within the mixture or separate. These particle size ranges can vary higher or lower depending on the application. At the time of use, the mixture is thawed by immersion in a warm water bath for 2-3 minutes at 37 degrees C. It is diluted in saline without spinning; and then the diluted mixture, with or without the bone blend being intermixed, can be implanted by packing, injection, scaffolding or any other suitable means into a patient.

Definitions

Bioenergetic—A process that promotes natural healing by creating harmony between the patient's body and the natural environment. Conducive to exchanges, flow and transformation of energy in and between living organisms and between living organisms and their environment.

Biologic Sumping—To drain, siphon or translate energy from a reservoir of collected biologic potential, in bone can be extracellular space surrounding cells that can be connected by haversian canals to support lymph, neural, and vascular conduits; last point of reserve within the source that can distributed or moved.

Cancellous Bone—refers to the relatively soft, spongy, trabeculated structures typically seen at the ends of bones and in vertebral bodies and other flat bones. Cancellous bone is marrow rich, and models under the dynamics of tension and compression.

Cortical Bone—dense outer surface of bone, aligned with compact lamellar processes that is richly mineralized and supports active osteocyte (bone cell) connections. Cortical bone also provides a protective environment for the inner endosteal package of bone marrow.

DBM—Demineralized Bone Matrix.

Elution—The washing out of a substance from a material into a fluid in which the material is immersed.

Freeze Dried/Lyophilized—Tissue dehydrated for storage by conversion of the water content of frozen tissue to a gaseous state under vacuum that extracts moisture.

Hydration—To supply water in order to restore or maintain fluid balance.

Magnetic Field—All moving charged particles produce magnetic fields. Moving point charges, such as electrons, produce complicated but well known magnetic fields that depend on the charge, velocity, and acceleration of the particles.

Negative pressure—pressure less than that of the surrounding atmosphere. Situation in which an enclosed volume has lower pressure than its surroundings. Any compromise in the divide between this area and the more highly pressurized area around it would cause substances to flow inwards, and equilibrate to net neutral conditions.

Normal Saline—0.9% Sodium Chloride Solution.

NTA—Nanoparticle Tracking Analysis. Used for determining size distribution and concentration of isolated exosomes by visualizing the light that is scattered from an exosome or microvesicle in liquid suspension. Particle size is calculated based on Brownian motion. NTA measures the size of individual exosomes as small as 30 nm.

PBS—Phosphate Buffered Saline.

PEF—Pulsed Electric Field—A specific non-magnetic device that generates competing signals of electric induction to achieve net "0" DC flow with alternating voltage spikes and decay. In some instances, the value of the interface leaves an asynchronous analog decay that has a signature null signal.

PEF—Plasmonic Exosome Fluorescence. Used for the analysis of extracellular lipid vesicles. Probes various substances by tightly confined electromagnetic field of surface plasmons. Sensing is based on surface plasmon resonance.

PEMF—Pulsed electromagnetic field. A frequency generator is used to energize coils to create a "pulsed" electromagnetic field. In 2004, a pulsed electromagnetic field system was approved by the FDA as an adjunct to cervical fusion surgery in patients at high risk for non-fusion. By 2007 the FDA had cleared several such stimulation devices.

Shockwave—a compressional wave of high amplitude caused by a shock (as from an earthquake or explosion) to the medium through which the wave travels. When a wave moves faster than the local speed of sound in a fluid it is a shock wave.

Tuned "physical chirality"—a symmetry property. The use of magnetic fields, shockwaves or pressure for the purpose of adjusting or aligning the chirality of existing molecules.

BRIEF DESCRIPTION OF THE DRAWINGS

The invention will be described by way of example and with reference to the accompanying drawings in which:

FIG. 36 is a depiction of intracellular attachment proteins, talin, change mechanical to chemical, integrins are pulled on.

DETAILED DESCRIPTION OF THE INVENTION

Figure 1:
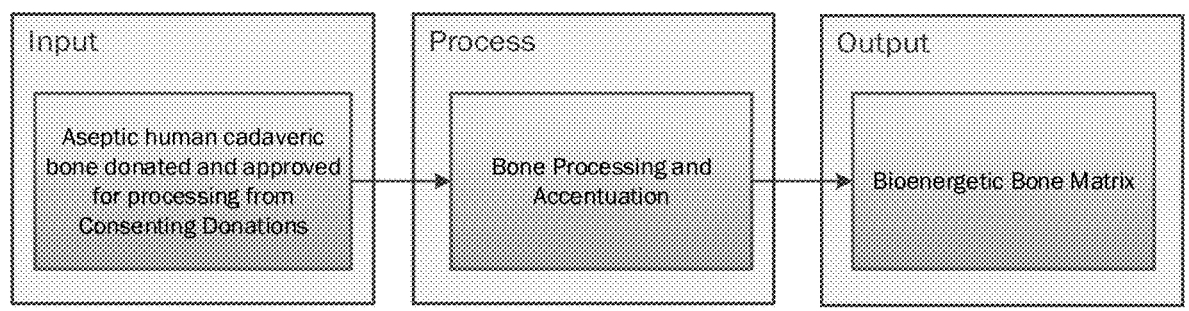
FIG. 1 is a flowchart depicting the overall bioenergetic bone matrix manufacturing process outline.
Figure 2:
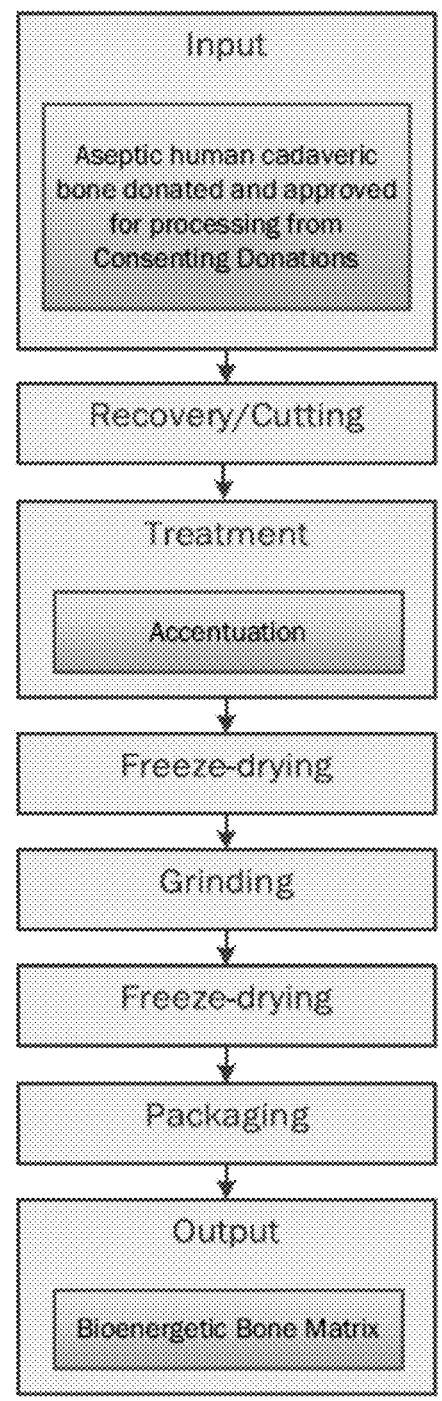
FIG. 2 is a flowchart depicting the Bioenergetic Bone Matrix Subprocess Flow.

The overall manufacturing process for the BioEnergetic Bone Matrix is depicted as an outline flowchart in FIG. 1 as well as FIG. 2. The input of the process is spinal columns from consenting donations, but can also include cortical bone prior to trimming, cutting, macerating, or demineralizing. Tissue processing achieves sufficient differences in matrix exosomes, in cell membrane and DNA packaging, and in the contents of the allograft, which at the most principal level is a biologic reservoir of tissue specific chemical matrices. A detailed description of the individual subprocesses can be found hereinafter.

All manufacturing, including recovery and further processing of the spinal column, is performed using aseptic technique. Samples are taken for microbiological cultures immediately after the excision of tissue to be used for processing of the components. All manufacturing prior to and during the packaging process is performed inside a monitored ISO Class 5 suite.

Figure 3:
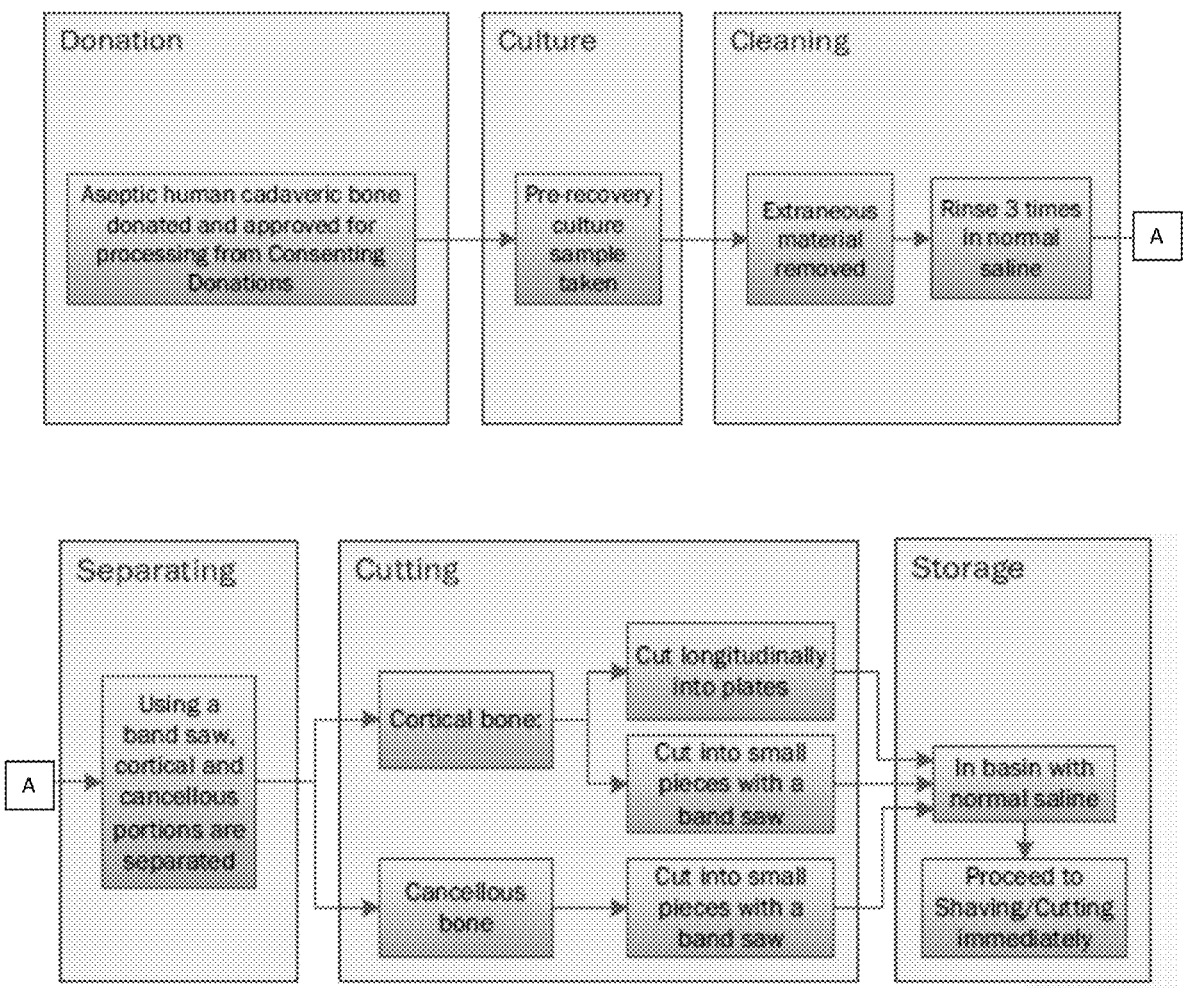
FIG. 3 is a flowchart depicting the recovery subprocess.

With reference to FIG. 3, in the recovery subprocess, prior to cutting the donated and approved for processing aseptic human cadaveric cortical and cancellous bone, all extraneous material such as muscle fibers, adipose tissue, and periosteum are removed from the tissue. Bones are then rinsed a minimum of 3 times with physiological grade normal saline (0.9% Sodium Chloride).

Various processes are used to stimulate the bone that have been shown in vitro to demonstrate a biological response. In particular, previous work using PEF with defined frequency distribution of 1.22 mV/cm$^2$ can be achieved by calculating the resistance of the solutions surrounding the biologic material and voltage adjusted accordingly. In previous work, conductivity of 83.5 ohm/cm was used to define volume, signal generation, and process time. No additional materials other than a wet holding solution are used in the process. Bone contained within individual containers, reflecting single donor identifiers, are processed overnight in biphasic voltages at 4.3 kZ at net "0" DC current.

Using a band saw, the bones are cut in a manner that the cortical and cancellous portions are separated. Cortical bone shafts are cut in half longitudinally and placed in basins with normal saline. Cancellous bone cut into pieces and crushed. Further cleaning and cutting of cortical and cancellous bone is as detailed below.

Figure 4:
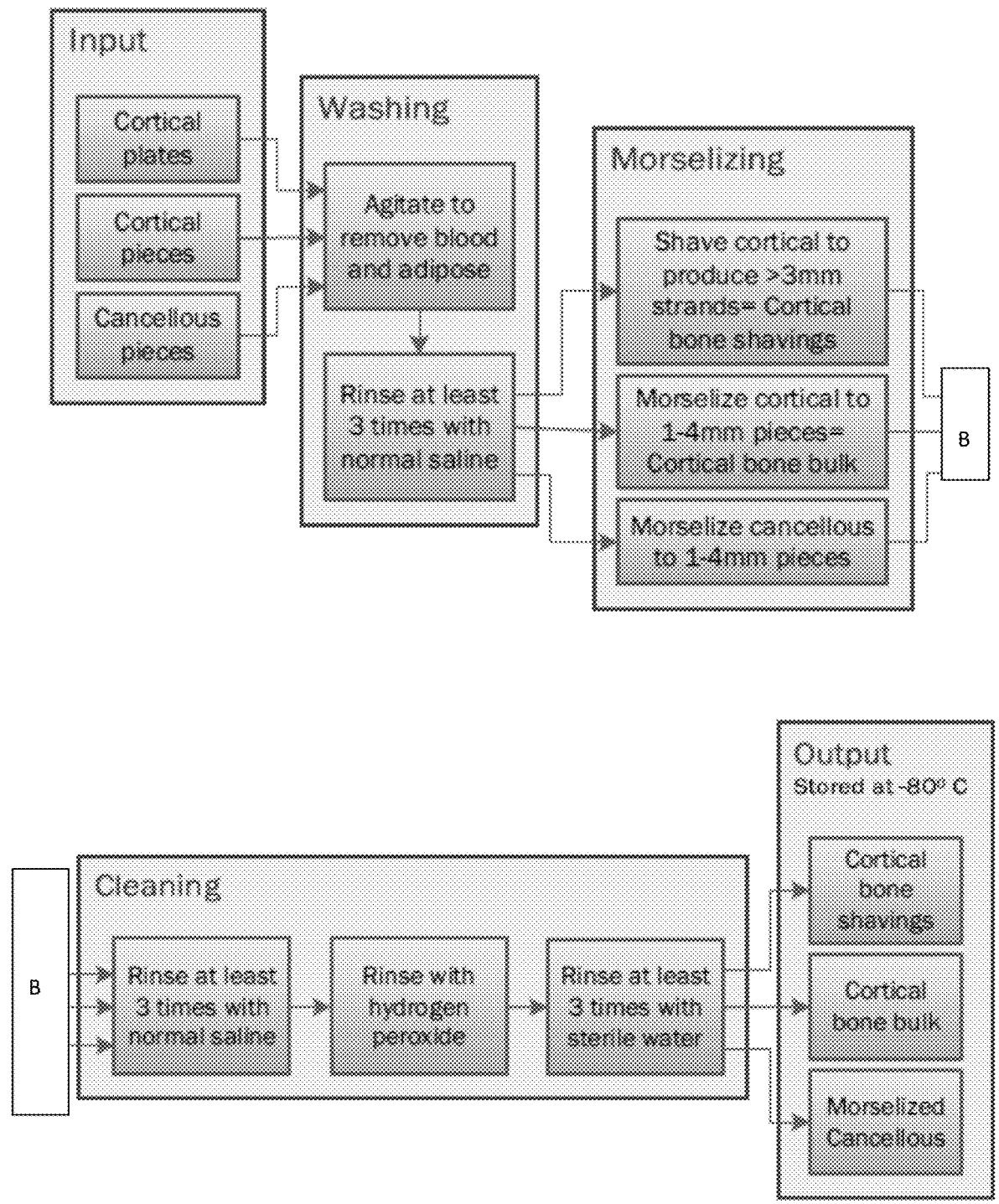
FIG. 4 is a flowchart depicting the shaving/cutting subprocess.

With reference to FIG. 4, in the Shaving/Cutting Subprocess for Cortical Bone Shavings, cortical bone plates are cut into approximately 6.5 cm long pieces. The bone plates are placed in a wash can with normal saline. The wash can is wrapped and agitated for 5 to 10 minutes to remove any blood and adipose tissue. Bone tissues are then rinsed with normal saline as often as needed to clean tissue of blood and/or fatty deposits. The bone tissues are shaved using a shaving machine set to produce >3 mm strands. Cortical bone shavings are collected in a basin and rinsed with hydrogen peroxide if required for no more than 10 minutes to remove fat/blood if necessary. Cortical bone shavings are rinsed a minimum of three times with sterile water to remove any residual hydrogen peroxide. The shavings are stored at −80° C.

For Cortical Bone Bulk, the cortical bone is then cut into small pieces using a band saw. The small pieces are rinsed a minimum of three times in Normal Saline and then placed into a metal container with fresh Normal Saline. The container is aseptically wrapped, placed on a shaker and mechanically agitated for 5 to 10 minutes. The bone tissue is then morselized into 1 to 4 mm length and width pieces, respectively, using a morselizer. The tissue is rinsed again a minimum of three times with Normal Saline in order to remove any remnants of blood and/or fat deposits. The bone pieces are rinsed with hydrogen peroxide for no more than 10 minutes to remove fat/blood. The bone pieces are rinsed a minimum of three times with sterile water to remove any residual hydrogen peroxide. Then, the bone tissue is placed in a metal container and stored at −80° C.

For Cancellous Bone, the cancellous bone is cut into small pieces using a band saw. The small pieces are rinsed a minimum of three times in normal saline and then placed into a metal container with normal saline. The container is wrapped, placed on a shaker and mechanically agitated for 5 to 10 minutes. The bone tissue is then crushed into approximately 1-4 mm pieces using a morselizer. The tissue is rinsed a minimum of three times with normal saline in order to remove any remnants of blood and/or fat deposits. The bone pieces are rinsed with hydrogen peroxide if required for no more than 10 minutes to remove fat/blood. The bone pieces are rinsed a minimum of three times with sterile water to remove any residual hydrogen peroxide. The cancellous bone tissue is placed in a metal cube and stored at −80° C.

Figure 5:
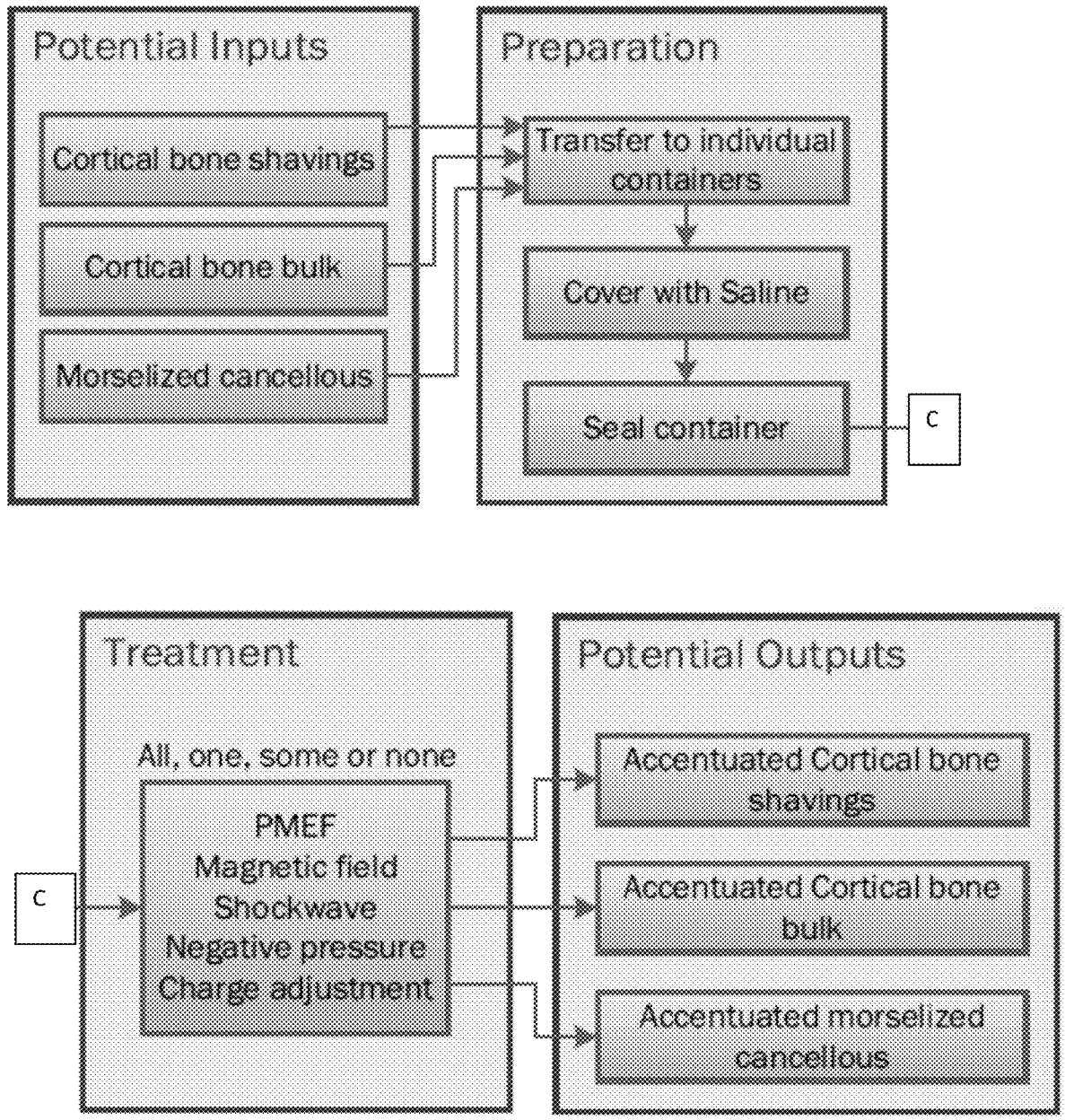
FIG. 5 is a flowchart depicting the enhancement subprocess.

With reference to FIG. 5, in the Enhancement subprocess, the cut, shaved, morselized or ground bone is suspended in enough saline to cover within a sealed polypropylene, polystyrene or Pyrex container. The container is exposed to a mechanical, atmospheric or membrane charge adjustment process. The time of exposure is to be optimized for each particulate configuration and enhancement process, and may include 0 minutes. Once the enhancement is complete, the saline is poured off, retaining the enhanced bone. Descriptions of enhancement processes utilized are described below: Saline decanted from processing may also be centrifuged that liquid portion collected and the macro, micro and nano solutes retained for the natural biologic cytokines inherent to this fraction.

PMEF (Pulsed ElectroMagnetic Field), a frequency generator is used to energize coils to create a "pulsed" electromagnetic field. The field is imposed across the containers diameter or length.

Magnetic Field, exposing the container to static, strong magnetic fields in a single direction across the diameter or length of the container.

Shockwave, a compressional wave of high amplitude is applied to the container. The shock wave will propagate through the medium; causing an abrupt, nearly discontinuous change in pressure, temperature and density of the medium.

Negative pressure, the use of shockwave causes changes in pressure of the medium to which it is applied. This may also be applied as its own treatment by creating a vacuum within the container using conventional technology, varying frequency and amplitude of stimulus or creating optimized algorithms that physically sustain appearance while offering cell stimuli consistent with regenerative inertia.

Charge Adjustment, the use of shockwave causes changes in pressure of the medium to which it is applied. This may also be applied as its own treatment by creating a vacuum within the processing container that can be accompanied by buffer, electric field, magnetic field or other physical inducements including gravity.

The process of enhancement should precede the processing as the goal is to stimulate the cells to expose exosomes, and attune genetic machinery to building bone. The intent is to encourage microRNA, and exosomal packages that are bone inductive, as well as for the machinery to translate proteins until the process is stopped for harvest and production.

Figure 6:
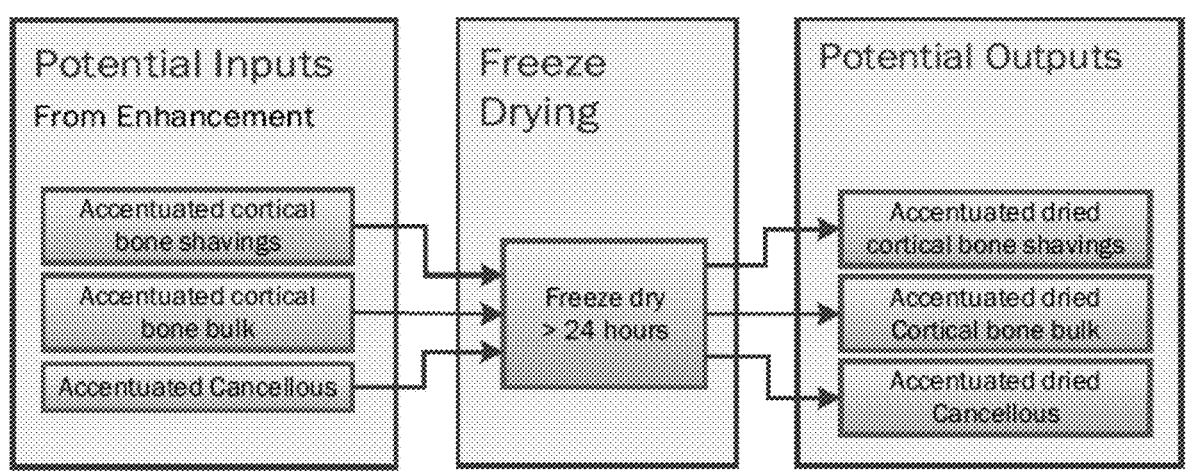
FIG. 6 is a flowchart depicting the freeze-drying subprocess.

With reference to FIG. 6, Freeze-drying subprocess #1, once the cortical bone shavings, bone bulk and morselized cancellous have been enhanced, it is then prepared to undergo the freeze drying process. The shavings, bulk and cancellous are placed in metal cubes on sterile drying trays. The drying trays are then placed inside of a freeze dryer which is set to run for greater than 24 hours. This cycle has shown to sufficiently dry the tissue without affecting the structural and chemical properties of the tissue.

Figure 7:
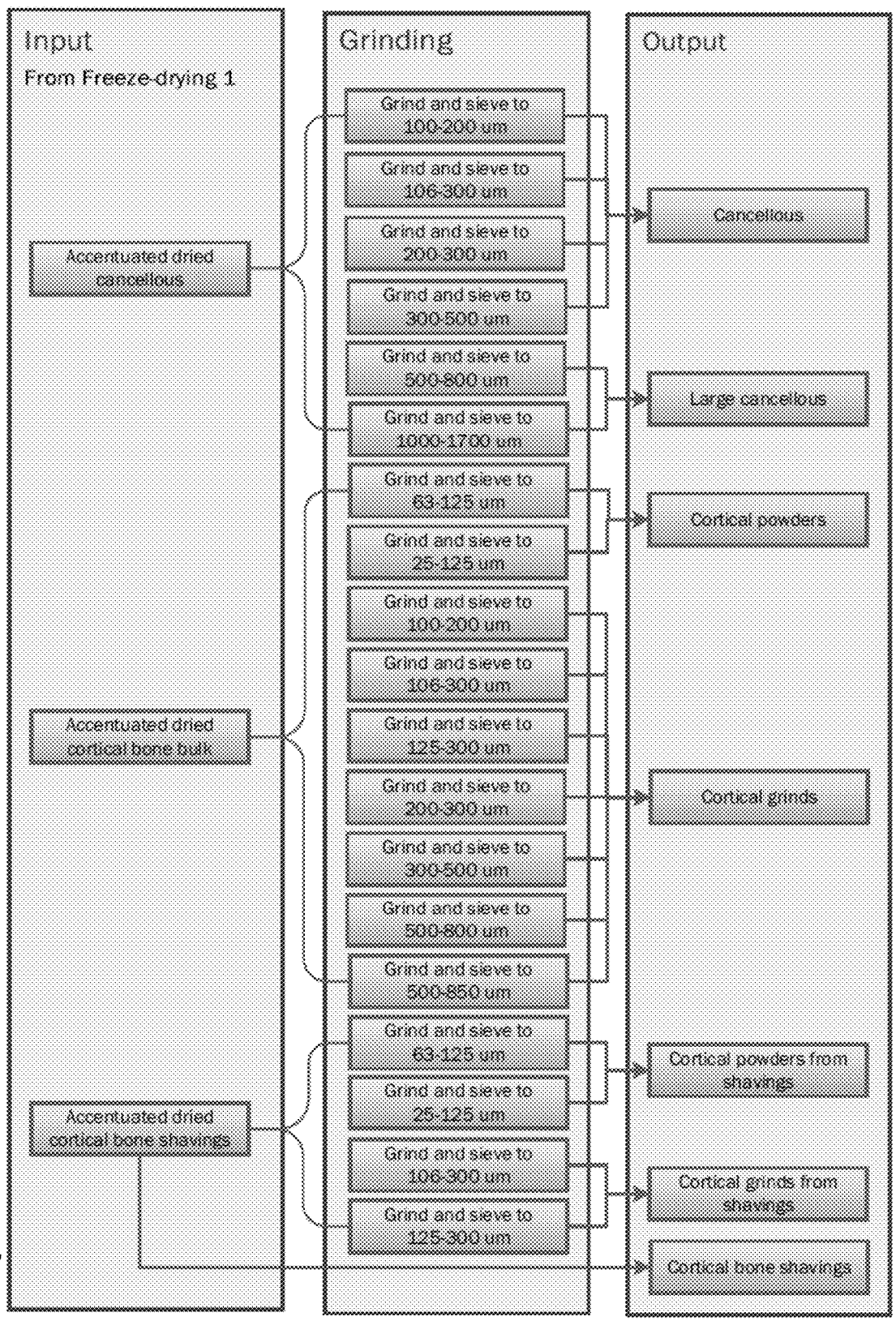
FIG. 7 is a flowchart depicting the grinding subprocess.

With reference to FIG. 7, Grinding subprocess for Cortical Bone Bulk: Grind and sieve to obtain particle sizes of 63-125 um. Grind and sieve to obtain particle sizes of 25-125 um. Grind and sieve to obtain particle sizes of 100-200 um. Grind and sieve to obtain particle sizes of 106-300 um.

Grind and sieve to obtain particle sizes of 125-300 um. Grind and sieve to obtain particle sizes of 200-300 um. Grind and sieve to obtain particle sizes of 300-500 um. Grind and sieve to obtain particle sizes of 500-800 um. Grind and sieve to obtain particle sizes of 500-850 um.

For Cortical Bone Shavings: Grind and sieve to obtain particle sizes of 63-125 um. Grind and sieve to obtain particle sizes of 25-125 um. Grind and sieve to obtain particle sizes of 106-300 um. Grind and sieve to obtain particle sizes of 125-300 um. Not ground, resulting in cortical shavings.

For Cancellous: Grind and sieve to obtain particle sizes of 100-200 um. Grind and sieve to obtain particle sizes of 106-300 um. Grind and sieve to obtain particle sizes of 200-300 um. Grind and sieve to obtain particle sizes of 300-500 um. Grind and sieve to obtain particle sizes of 500-800 um. Grind and sieve to obtain particle sizes of 1000-1700 um.

Figure 8:
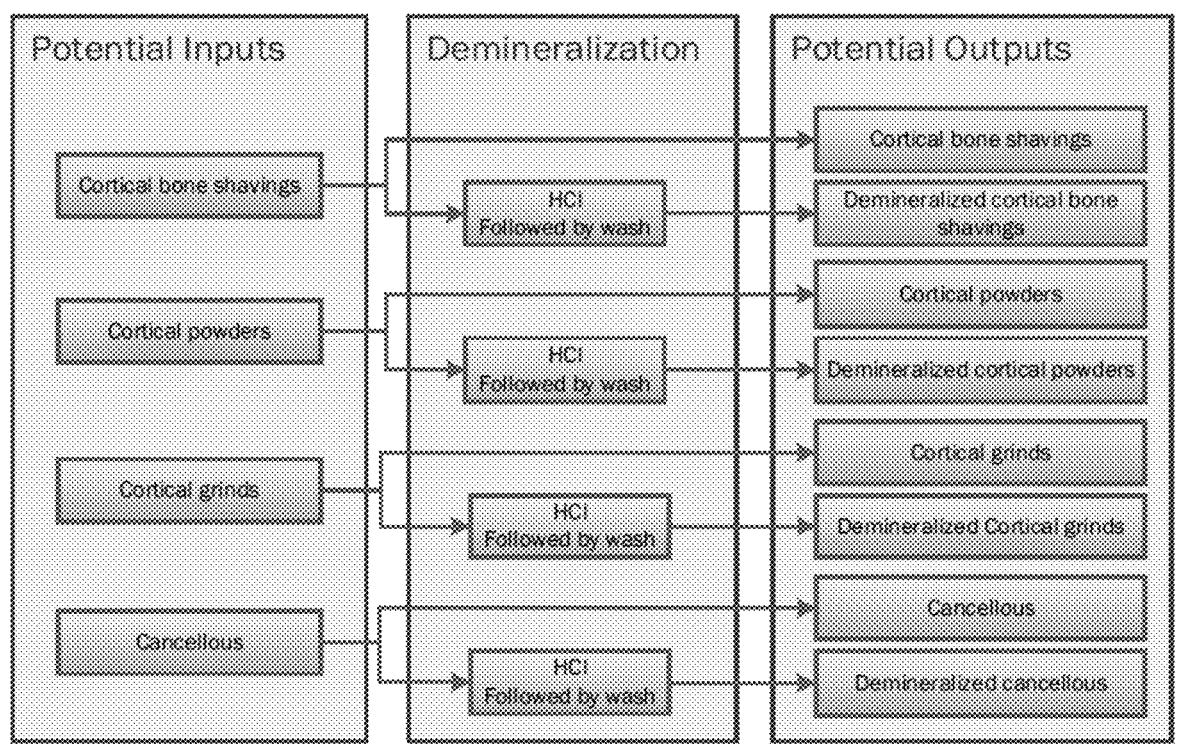
FIG. 8 is a flowchart depicting the demineralization subprocess.

With reference to FIG. 8, Demineralization subprocess for Cortical Bone Shavings, cortical bone shavings which are meant to be demineralized are mixed with HCL solution for full or partial demineralization. The solution containing the tissue is placed on a magnetic stir plate for a predetermined number of minutes. After decanting the liquid, the particulate tissue is mixed with sterile water at a 20:1 ratio (20 ml of sterile water to 1 g of bone). The solution containing the tissue is placed on a magnetic stir plate. The process of decanting, mixing and stirring is repeated with PBS solution. After decanting the PBS, the shavings are mixed with sterile water at a 20:1 ratio (20 ml of sterile water to 1 g of bone). The solution containing the tissue is placed on a magnetic stir plate to mix. The water waste solution is decanted and the demineralized shavings are stored at −80° C. The intention of the process of washing carries with it the intention and potential for retaining the wash solutions, reducing the aqueous areas and concentrating sub cellular fractions of materials inherent to compositions of bone that might be lost because of size. This present invention recognizes previous shortcomings of processes that have inadvertently disposed of small-sized, biologically active components. By intention, these fractions are known to broadly offer "paracrine" function and more specifically participate in restorative dynamics of the regenerative process.

Cortical Powders, any cortical powders which are meant to be demineralized are mixed with HCL solution for full or partial demineralization. The solution containing the tissue is placed on a magnetic stir plate for a predetermined number of minutes. After decanting the liquid, the particulate tissue is mixed with sterile water at a 20:1 ratio (20 ml of sterile water to 1 g of bone). The solution containing the tissue is placed on a magnetic stir plate. The process of decanting, mixing and stirring is repeated with PBS solution. After decanting the PBS, the shavings are mixed with sterile water at a 20:1 ratio (20 ml of sterile water to 1 g of bone). The solution containing the tissue is placed on a magnetic stir plate to mix. The water waste solution is decanted and the demineralized shavings are stored at −80° C.

Cortical Grinds, any cortical grinds which are meant to be demineralized are mixed with HCL solution for full or partial demineralization. The solution containing the tissue is placed on a magnetic stir plate for a predetermined number of minutes. After decanting the liquid, the particulate tissue is mixed with sterile water at a 20:1 ratio (20 ml of sterile water to 1 g of bone). The solution containing the tissue is placed on a magnetic stir plate. The process of decanting, mixing and stirring is repeated with PBS solution. After decanting the PBS, the shavings are mixed with sterile water at a 20:1 ratio (20 ml of sterile water to 1 g of bone). The solution containing the tissue is placed on a magnetic stir plate to mix. The water waste solution is decanted and the demineralized shavings are stored at −80° C.

Cancellous, any cancellous which is meant to be demineralized is mixed with HCL solution for full or partial demineralization. The solution containing the tissue is placed on a magnetic stir plate for a predetermined number of minutes. After decanting the liquid, the particulate tissue is mixed with sterile water at a 20:1 ratio (20 ml of sterile water to 1 g of bone). The solution containing the tissue is placed on a magnetic stir plate. The process of decanting, mixing and stirring is repeated with PBS solution. After decanting the PBS, the shavings are mixed with sterile water at a 20:1 ratio (20 ml of sterile water to 1 g of bone). The solution containing the tissue is placed on a magnetic stir plate to mix. The water waste solution is decanted and the demineralized shavings are stored at −80° C. In all cases, the function of retaining wash solutions is accepted as a means of collecting small, low molecular weight fractions of allogeneic materials.

Figure 9A:
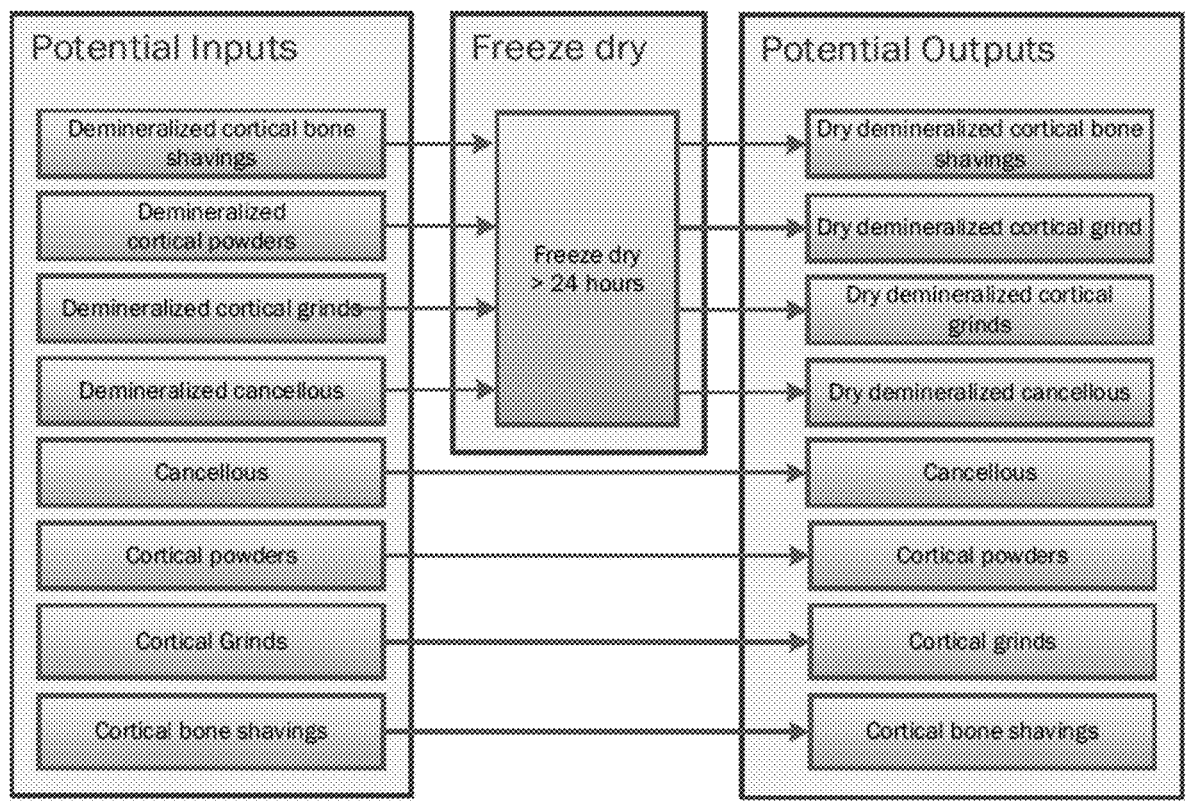
FIGS. 9A and 9B show a flowchart depicting the second freeze-drying subprocess.
Figure 9B:
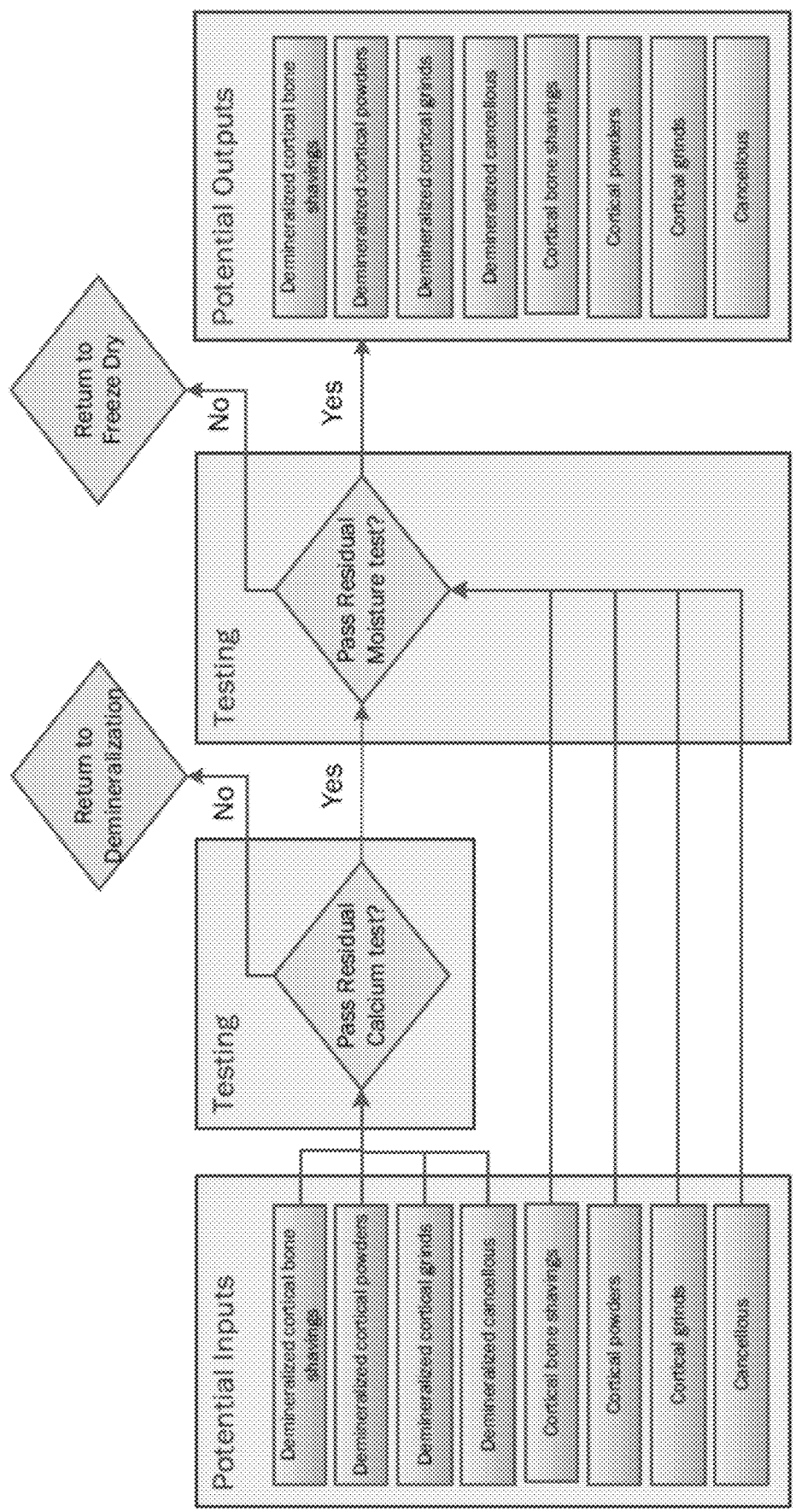

With reference to FIGS. 9A and 9B, Freeze-drying subprocess #2, the demineralized cortical bone particulates are then prepared to undergo the freeze-drying process again. The grind or shavings are placed on sterile drying trays. The drying trays are then placed inside of a freeze dryer which is set to run for greater than 24 hours. This cycle has shown to sufficiently dry the tissue without affecting the structural and chemical properties of the tissue.

Figure 10A:
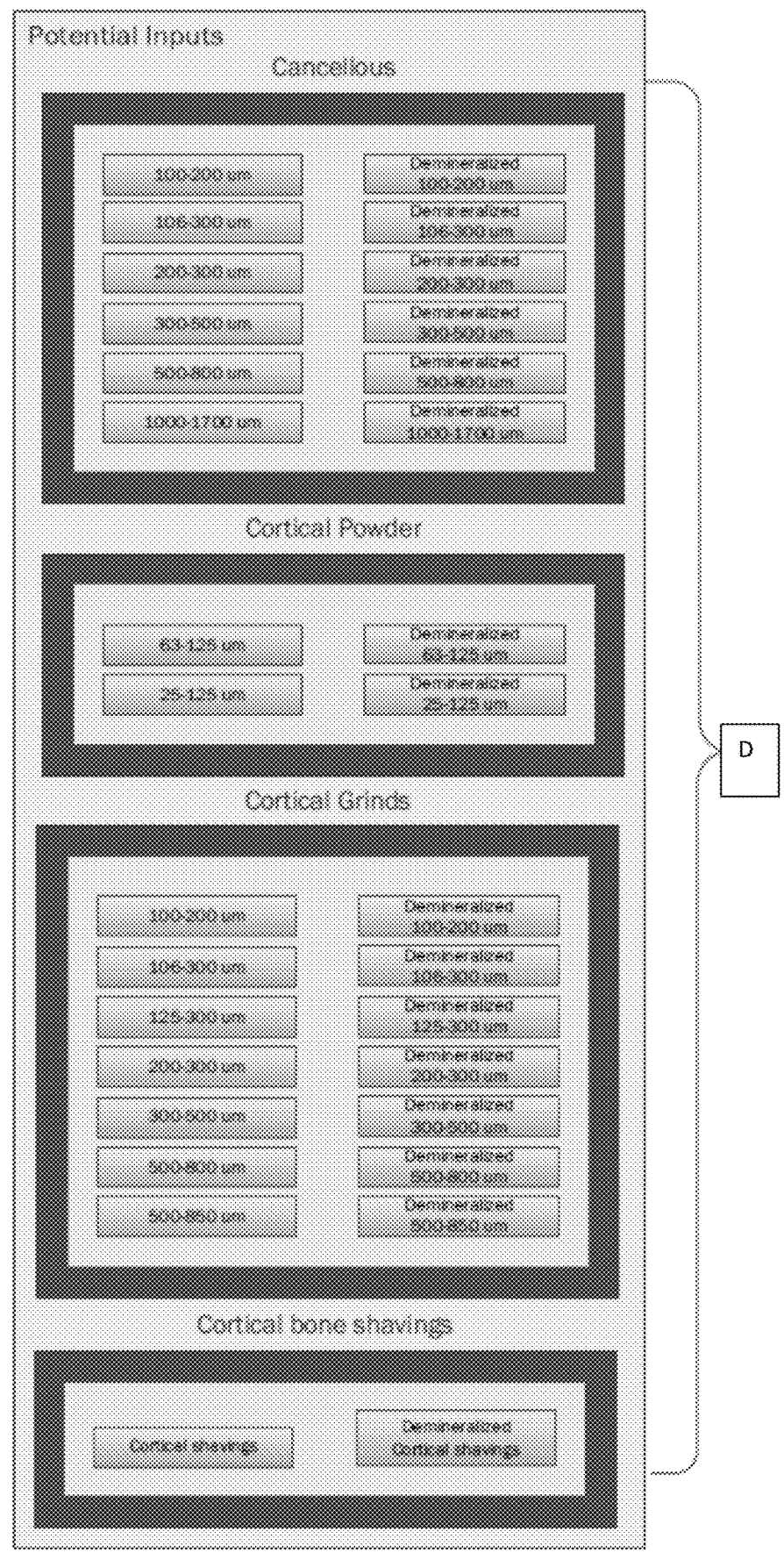
FIGS. 10A and 10B show a flowchart depicting the packaging subprocess.
Figure 10B:
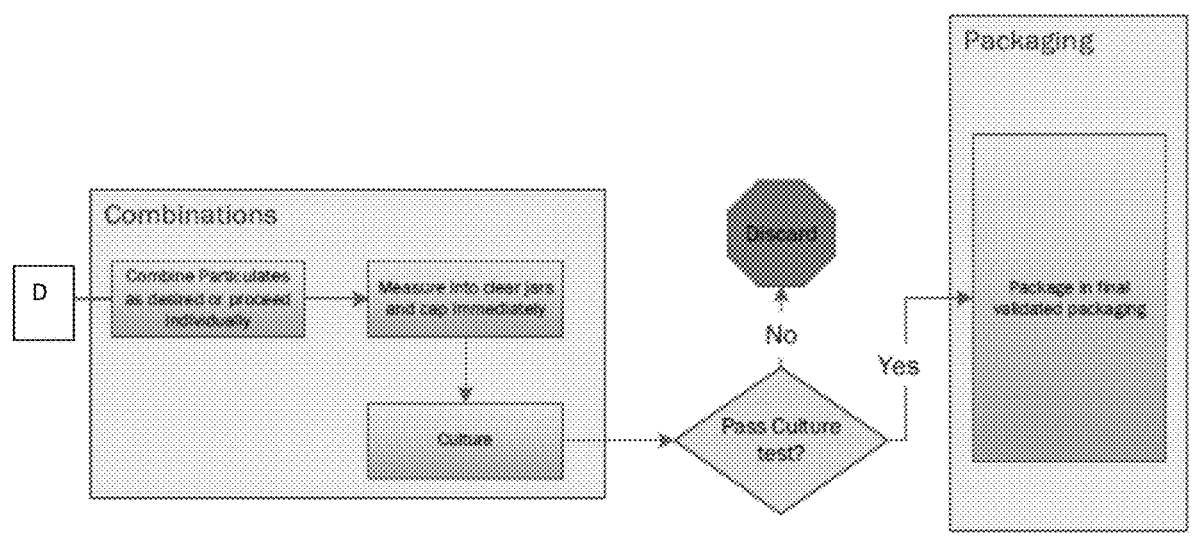
Figure 11:
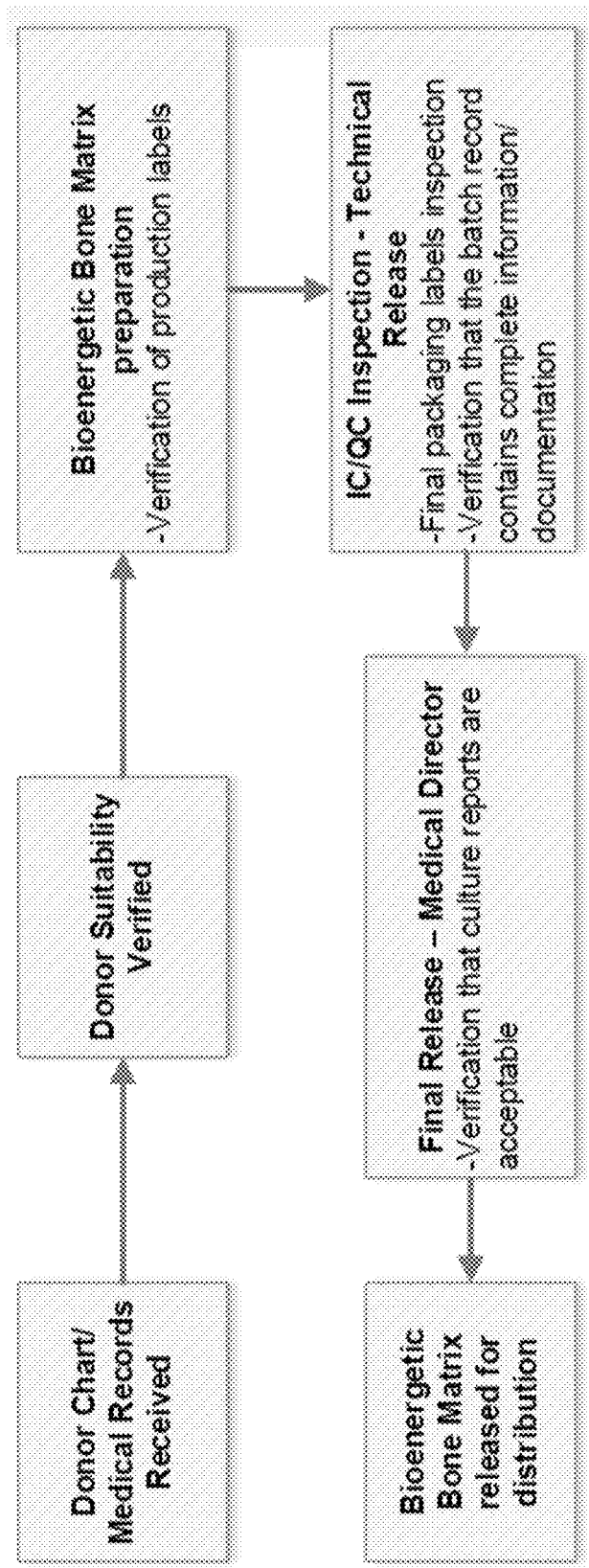
FIG. 11 is a flowchart depicting the quality subprocess.

With reference to FIGS. 10A and 10B, Packaging subprocess, final processed mineralized and demineralized cortical shavings and particulate, crushed cancellous and cortical powder are combined as appropriate and packaged in validated final packaging. The mixtures are aseptically measured into jars; each jar closed tightly. The outer packaging used is a chevron type pouch allowing the end user to easily present the sterile inner pouch containing the product to a sterile field. The packaged final product is stored at room temperature to −80 C, depending on coexisting products, until it is distributed to the end user. Batch release is contingent upon final culture results. FIG. 11 details the quality subprocess.

Figure 12:
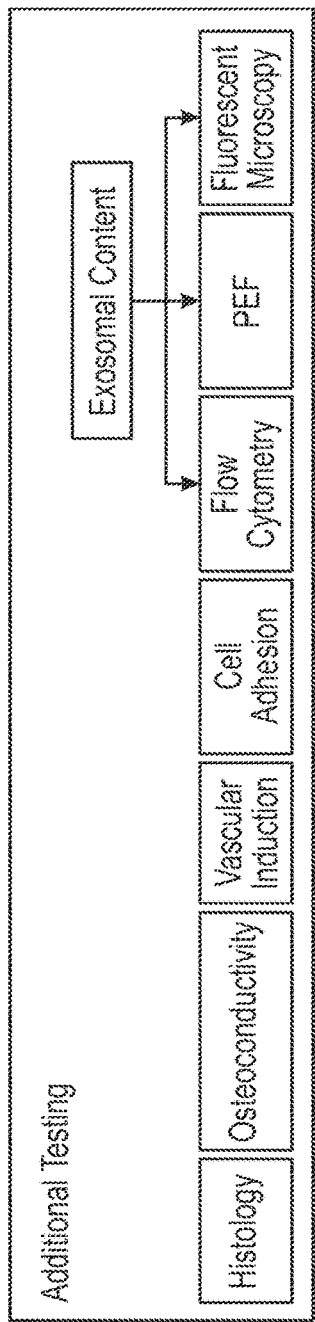
FIG. 12 is a flowchart depicting the validation subprocess.

FIG. 12 shows the Validation subprocess, Final processed, combined, mineralized and demineralized cortical shavings, particulate, powder, and cancellous are tested for residual moisture and Residual Calcium. The following tests may also be imposed as a continuation of data collection and further validation.

Residual Moisture will be tested according to standard operating procedures.

Residual Calcium will be assessed by standard outsourced testing.

Utilizing plasmonic exosome fluorescence, PEF, exosome concentration will be measured by binding to the sensor surface which contains an array of periodic nanoholes patterned in a metal film. The binding is monitored through change in optical transmission due to change of refractive index at the sensor surface.

NTA allows exosomes to be counted and sized by combining light microscopy and software that tracks Brownian motion of exosomes. The light scattering mode is used to measure size. Extracted CD63+ exosomes will be visualized and quantified in combination with fluorescent markers utilizing NTA with a NanoSight instrument.

Osteoinductivity will be assessed by standard outsourced testing (C2C12 method).

Cell adhesion will be assessed by combination of L929 and MSCs with the Bioenergetic bone. 72 hour culture at 370 C followed by fixation, staining, fluorescent microscopy and histology will verify cell attachment to the Bioenergetic particulate.

Vascular induction or inductability will be assessed by VEGF-A MagPix multiplex assay of conditioned media from MSCs attached and grown for 48 hours on Bioenergetic particulate.

Percent CD63+/wt will be assessed by CD63 antibody pulldown from enriched collection of digested product. Exosomes will be enriched from the digested product and magnetically separated and purified on beads. FITC-conjugated antibody will allow quantification of CD63+ beads. Percent CD63+ exosomes will be calculated as a function of particulate weight.

Fluorescent microscopy with CD63 antibody staining in combination with DAPI and propidium iodide will show localization of exosomes relative to dehydrated cells and matrix.

Enhanced Bioenergetics includes Tuned chirality, moving point charges, such as electrons, produce complicated but well known magnetic fields that depend on the charge, velocity, and acceleration of the particles. The result of exposure to strong magnetic fields is to change the magnetization of any material within the magnetic field and affect the organization of the particles through chiral tuning and electron cloud polarization.

Magnetic fields, shockwaves or pressure adjust or align the chirality of existing molecules. Tuning of chirality in nonorganic and organic substances is known to affect the interaction and adhesion properties of the molecules. Many biologically active molecules are chiral, including the naturally occurring amino acids.

Exosome content, Magnetic fields, shockwaves or pressure enhance the shedding of exosomes and microvesicles. These acellular components are known to represent the cell phenotype and signaling from which they arose. Increasing the concentration of these subcellular and acellular components as more readily available signaling adjuncts enriches the particulate in determinate capacity. The manufacturing process has been designed to capture fractions of biologic materials that have been traditionally discarded as wash solution decants.

Circulating currents in the body have differential biological effects on bone healing and nerve stimulation based on the induced current density. The use of 1 to 1000 mA/m2 PEMF promotes exosome and microvesicle shedding in cells, enhancing the deliverable signals within the bone. This enhancement is maintained during the processing of the bone to particulate.

The use of shockwaves has been shown to condition the media in which the cells are suspended with microvesicles and exosomes. Media conditioned with shockwave treated cells positively affects the cells count and viability of target cells as shown below.

Additionally, the increased concentration of exosomes, microvesicles and available signaling molecules shed from the particulate contains specific osteoinductive signals inherent in the donor bone before processing.

The decreased pressure removes atmospheric pressures against proprioceptors, inflicting a false sense of non-attachment. This informs the microenvironment that it is not in a position to attach, differentiate or proliferate. The intended effect is that of non-stress. Any compromise in the pressurized area would cause substances to flow inwards, resulting in increased hydration and activation of contact responsive receptors (proprioceptors) due to the sharp increase in density. Additionally, the sensing of stress in the environment induces shedding of microvesicles, exosomes, etc.

Osteoinductivity, the demineralization process of bone tissue exposes morphogenetic proteins and other intrinsic growth factors involved in providing the osteoinductive signal to form new bone. The tuning of chirality, which increases adhesion properties, increases the endogenous MSC adhesion-responsive differentiation to bone. Any added factors combined with the same particulate is equally affected. Additionally, the increased concentration of exosomes, microvesicles and available signaling molecules shed from the particulate contains specific osteoinductive signals inherent in the donor bone before processing.

In addition to osteoinductivity, the tuning of chirality, which affect the interaction and adhesion properties of the molecules within the particulate, increases the structural organization, resulting in increased osteoconductivity. Recipient MSC's and osteoprogenitors benefit from and respond positively to the enhanced structural organization.

As presented above, tuning of chirality in nonorganic and organic substances is known to affect the interaction and adhesion properties of the molecules. This effect increases the structural organization. Cell adhesion is therefore increased.

Shockwave treatment of cells affects the morphology of cells by the pulling or breakage of adherins and integrins. This has profound effects on the adhesion of the cells to the parent bone cells.

Negative pressure (decreased compared to outside) removes atmospheric pressures against proprioceptors, inflicting a false sense of non-attachment. Such a microenvironment alters cell perception as to ques to attach, differentiate or proliferate. The intended effect is that of non-stress. Any compromise in the pressurized area would cause substances to flow inwards, resulting in increased hydration and activation of contact responsive receptors (proprioceptors) due to the sharp increase in density.

Directed Morphology and phenotype, since exosomes, microvesicles and other components shed during treatment are representative of the cell from which they arose, use of the presented enhancements provides signaling that promotes the morphology and phenotype of the source cells.

Shockwave stimulation on cells has multiple effects on the landscape of the cells, as well as the signaling that occurs from and within that cell. The morphology is affected by the pulling or breakage of adherins and integrins. Changes in morphology (shape), revealing of sites for signaling and changes in enzyme activity are representative of the directed phenotype subsequent to pressure variations.

Lateral transfer of genetic material, exosomes, microvesicles and other components shed during treatment contain representative DNA, RNA and proteins of the source cell. Increased concentration of these components promotes lateral signaling, including but not limited to: access by endocytosis or passive entry to recipient cells, extracellular and intracellular receptor activation or inactivation through multiple mechanisms. Such mechanisms may include translation of provided genetic material, modification of resident proteins by provided enzymes or binding factors, binding to receptors, cleavage of receptors, RNA binding for activation or inactivation and DNA binding for activation or inactivation. All such activities represent the promotional activities of the source cell. In the case of the treatments presented here, the source cells are those resident in cortical or cancellous bone isolated from vertebral bodies.

Stress response, it is known that pH changes induce cellular stress. As a response to stress, cells shed exosomes, microvesicles and other components. Additionally, there have been studies showing that pH shock induces a stem cell response in the cells, and it is well understood that pH domain specifically guard against differentiation. Such retention of pluripotency is considered an asset of this process.

Bilayers are made of two layers of amphiphile molecules which possess a charged hydrophilic head and a hydrophobic tail. The density and arrangement of the molecules within the membrane determine the membrane's porosity, strength, and other properties. Most molecules in the membrane do not respond to a change in acidity. For the molecules that are affected, the charge of the molecules' heads change in that their two-dimensional crystallization morphs from a rectangular-patterned lattice (basic solutions) to a hexagonal lattice (acidic solutions). Membranes with a higher symmetry, such as hexagonal, are stronger and less brittle than those with lesser symmetry.

The change in pH also alters the bilayers' thickness and the compactness of the molecules. Changing the density and spacing of molecules within membranes helps control the encapsulation and release efficiency of molecules inside a vesicle.

Charge adjustment causes an immediate increase in perinuclear vesicles which are lipid rich, can be extracted and maintain their identity (Mackenzie 1961).

Negative pressure informs the microenvironment that it is not in a position to attach, differentiate or proliferate. The intended effect is that of non-stress. Any compromise in the pressurized area causes substances to flow inwards, resulting activation of contact responsive receptors (proprioceptors) due to the sharp increase in density.

These factors combined, and individually, promote the osteoinductive capacity of enhanced particulate.

Figure 13:
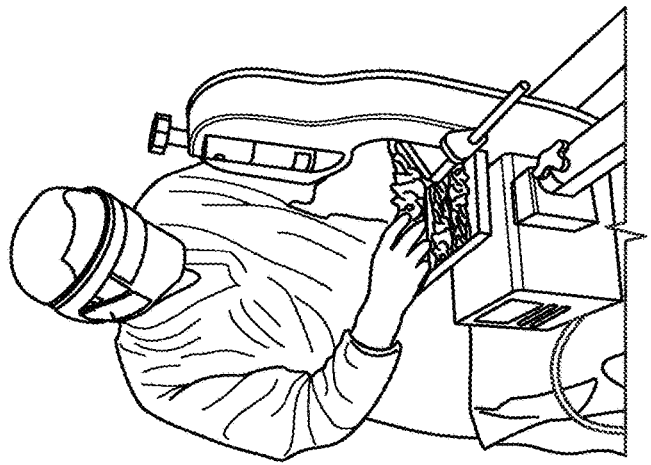
FIG. 13 is a photograph showing the cutting of vertebral column to isolate vertebral bodies.

FIG. 13 is a photograph showing the cutting of vertebral column to isolate vertebral bodies.

Figure 14:
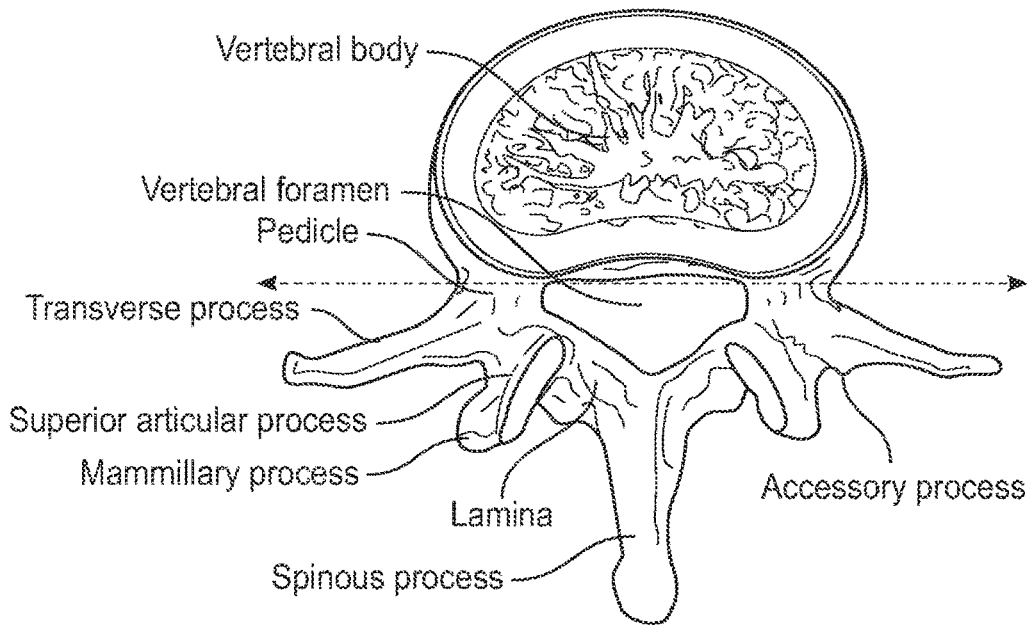
FIG. 14 is a depiction of an illustration of the removal of processes and extraneous material.

FIG. 14 is a depiction of an illustration of the removal of processes and extraneous material from a vertebral body.

Figure 15:
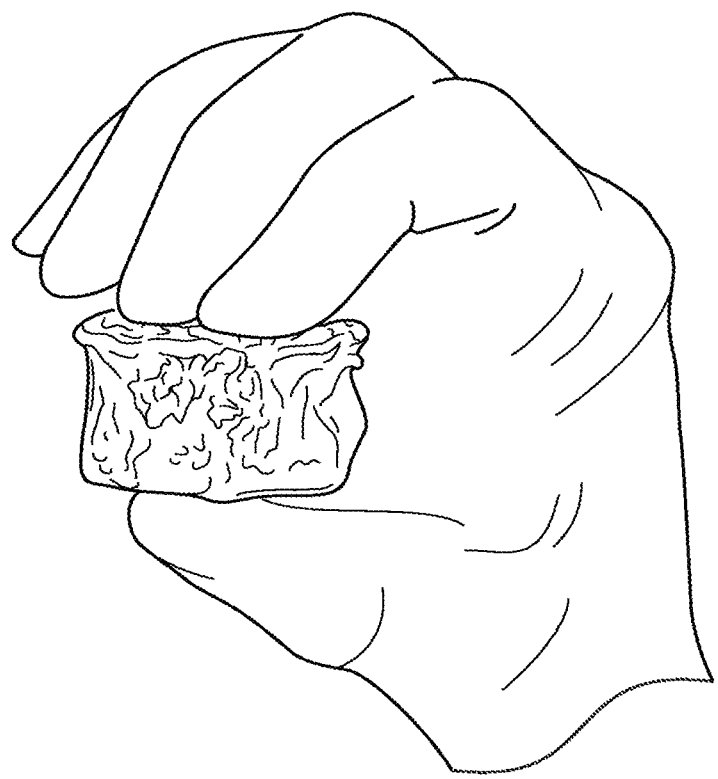
FIG. 15 is a photograph showing the recovered vertebral body, ready for cutting.

FIG. 15 is a photograph showing the recovered vertebral body, ready for cutting.

Figure 16:
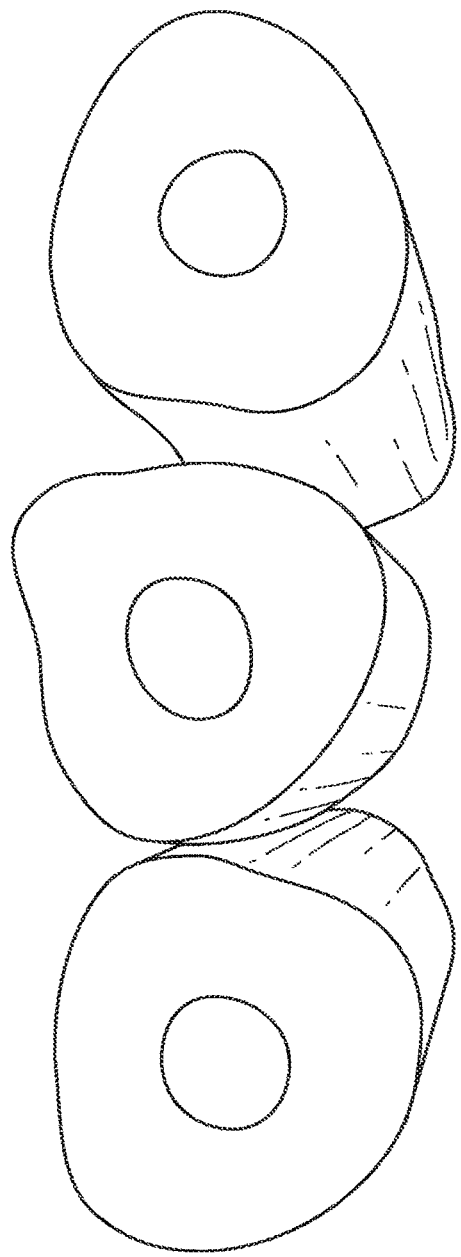
FIG. 16 is a photograph of recovered cortical bone, ready for cutting or shaving.

FIG. 16 is a photograph of recovered cortical bone, ready for cutting or shaving.

Figure 17:
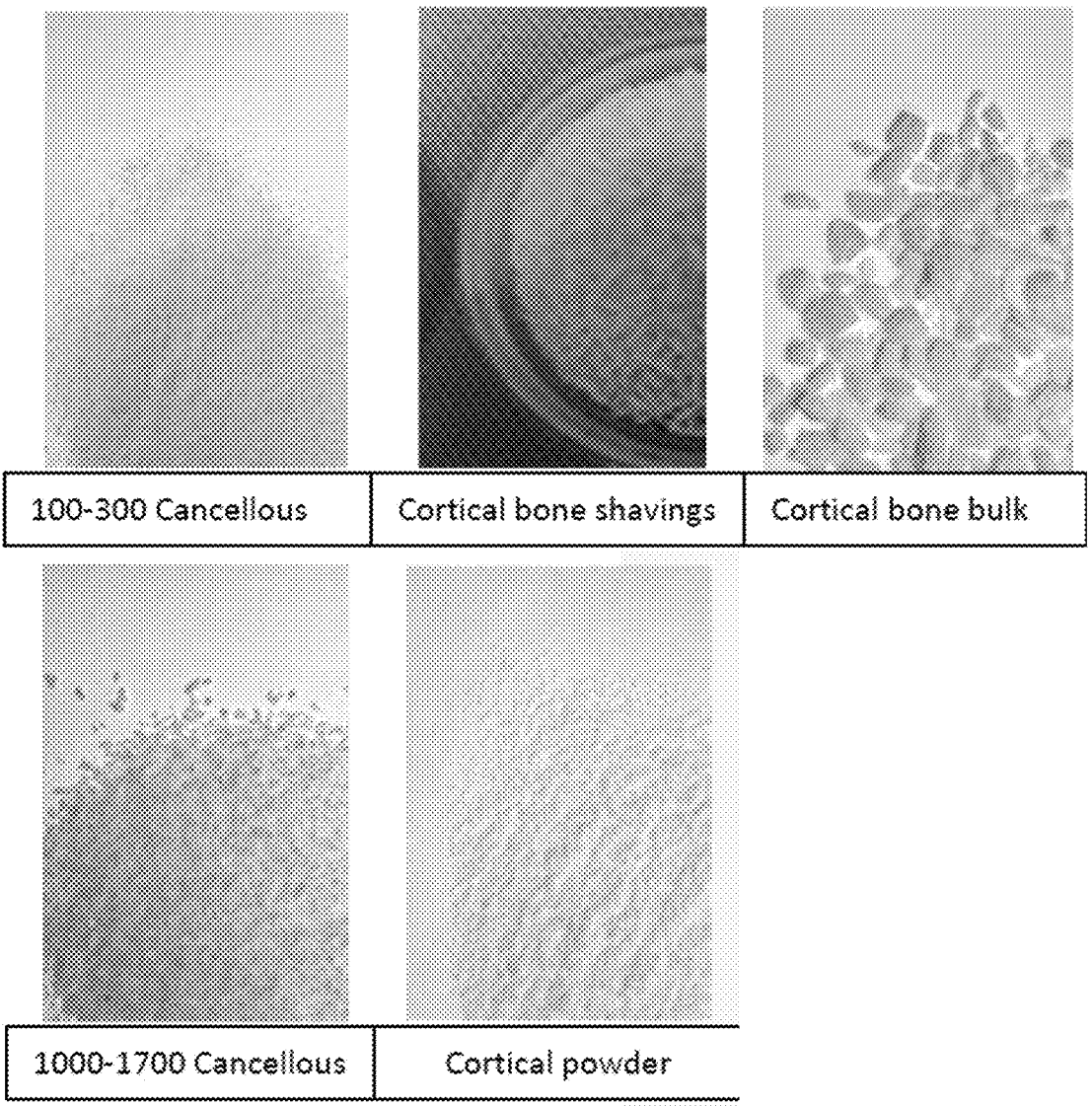
FIG. 17 is a series of photographs showing shaving/cutting options.

FIG. 17 is a series of photographs showing shaving/cutting options.

Figures 18, 19:
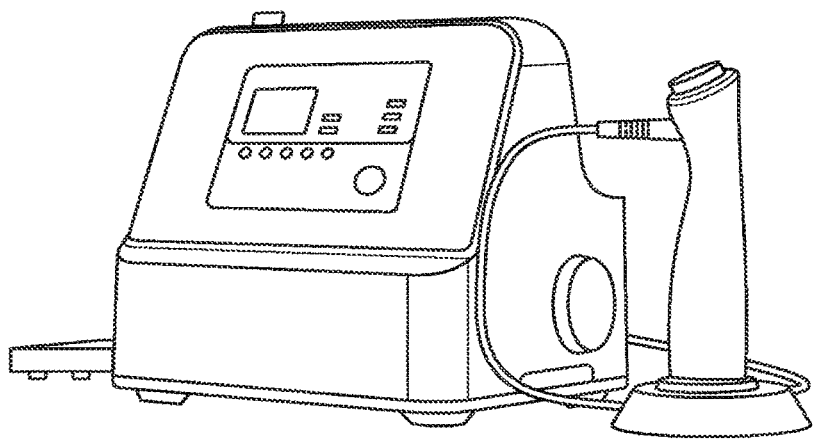
FIG. 18 is a picture of a representative magnetic field generator.
FIG. 19 is a chart showing the threshold values of ELF induced current densities for producing biological effects.

FIG. 18 is a picture of a representative magnetic field generator.

FIG. 19 is a chart showing the threshold values of ELF induced current densities for producing biological effects.

Figures 20, 21:
FIG. 20 is a graph of shockwave related items.
FIG. 21 is a photograph of particulate after freeze-drying.

FIG. 20 is a graph of shockwave related items described in https://jtultrasound.biomedcentral.com/articles/10.1186/s40349-016-0053-z.

FIG. 21 is a photograph of particulate after freeze-drying.

Figure 22:
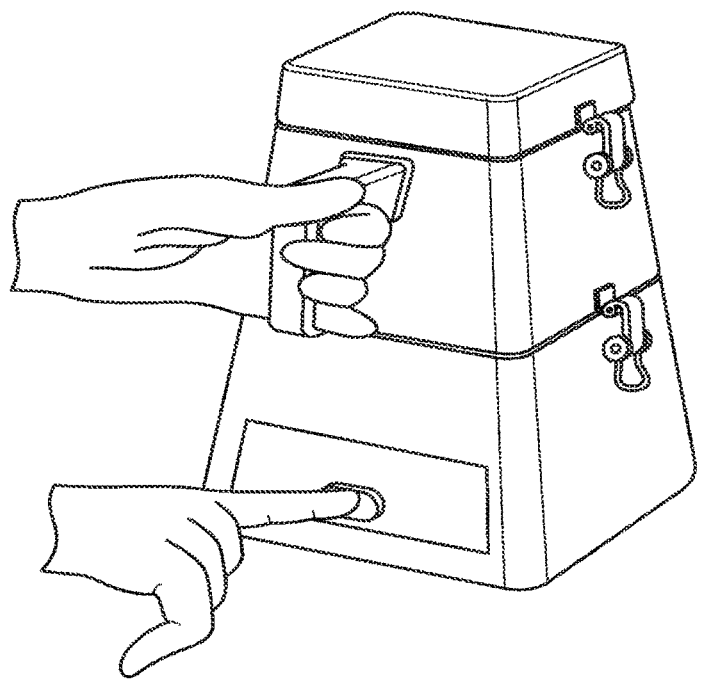
FIG. 22 is a photograph of a representative grinder for creating particulates.

FIG. 22 is a photograph of a representative grinder for creating particulates.

Figure 23:
FIG. 23 is a photograph of a representative sieve for selecting particle sizes.

FIG. 23 is a photograph of a representative sieve for selecting particle sizes.

Figure 24:
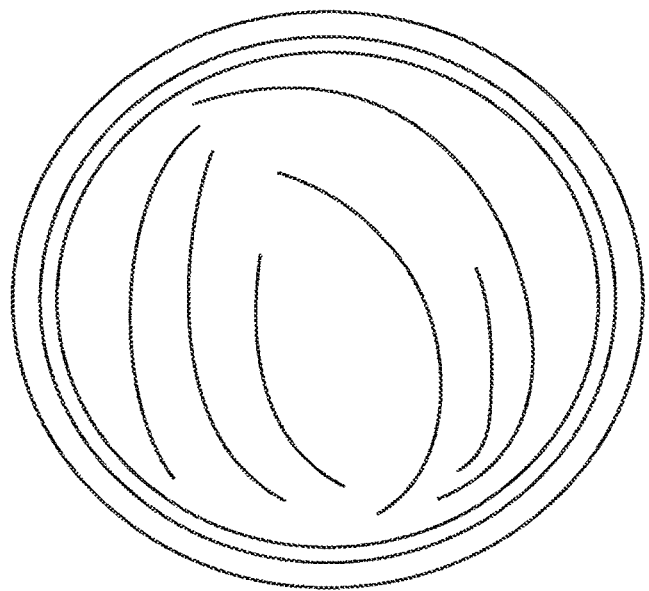
FIG. 24 is a photograph of different sizes of particulates.

FIG. 24 is a photograph of different sizes of particulates.

Figure 25:
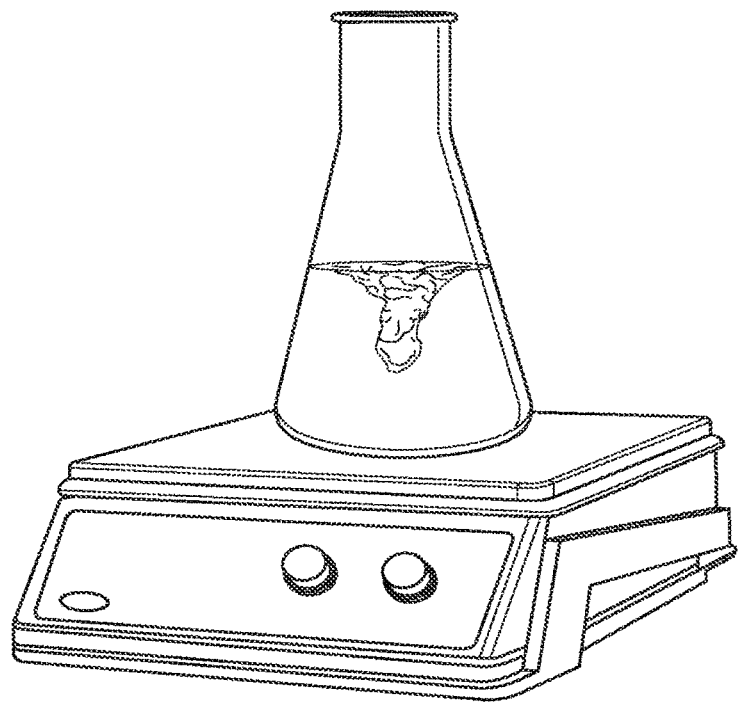
FIG. 25 is a representative picture of a large flask with diluted HCl for addition of particulate.

FIG. 25 is a representative picture of a large flask with diluted HCl for addition of particulate.

Figure 26:
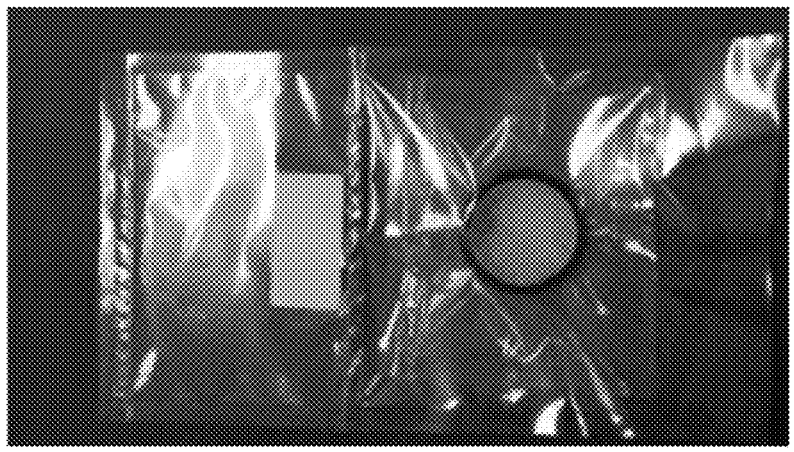
FIGS. 26-28 are a set of photographs showing how the particulate may be packaged individually or with other products.
Figure 27:
Figure 28:

FIGS. 26-28 are a set of photographs showing how the particulate may be packaged individually or with other products.

Figure 29:
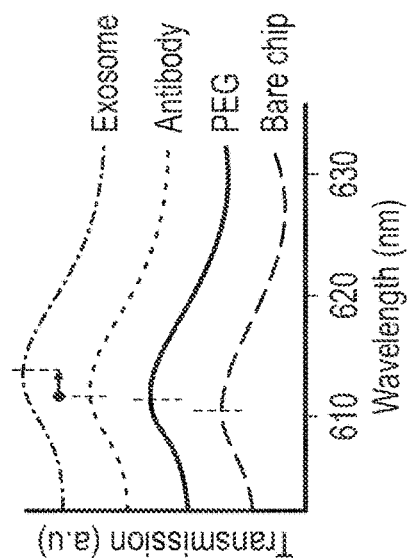
FIG. 29 is a set of pictures of the PEF grid, exosomes collected on the grid and representative data.
Figure 29:
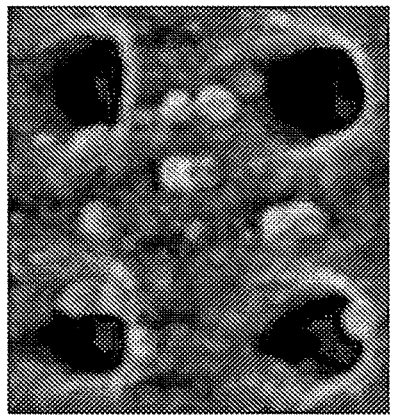
Figure 29:
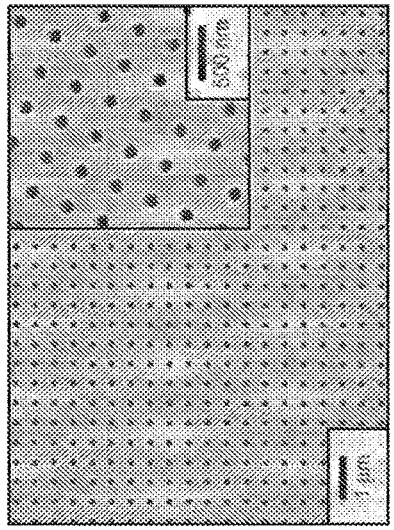

FIG. 29 is a set of pictures of the PEF grid, exosomes collected on the grid and representative data from.

Figure 30:
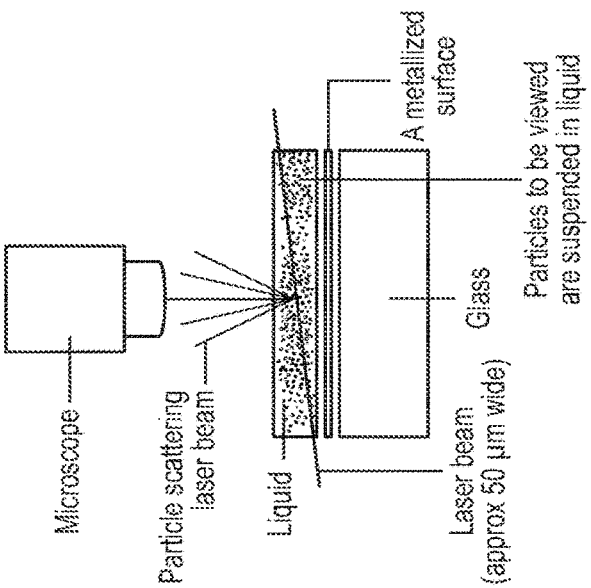
FIG. 30 is a set of pictures showing exosomes particle tracking, fluorescent visualization with size distribution and descriptive picture of NTA process.
Figure 30:
Figure 30:
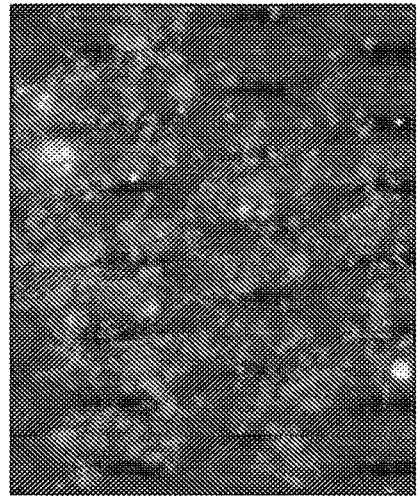

FIG. 30 is a set of pictures showing exosomes particle tracking, fluorescent visualization with size distribution and descriptive picture of NTA process from http:www.genengnews.com/media/images/article/Nanosight.

Figure 31:
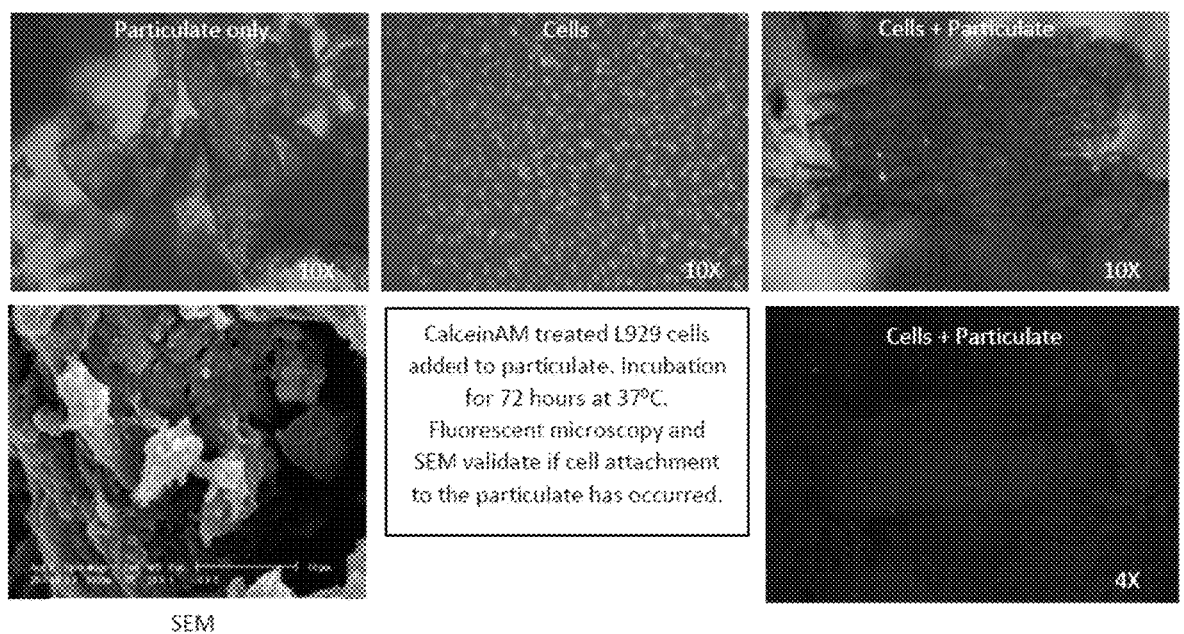
FIG. 31 is a set of pictures showing CalceinAM treated L929 cells added to particulate. Incubation for 72 hours at 370 C. Fluorescent microscopy and SEM validate if cell attachment to the particulate has occurred.

FIG. 31 is a set of pictures showing CalceinAM treated L929 cells added to particulate. Incubation for 72 hours at 370 C. Fluorescent microscopy and SEM validate if cell attachment to the particulate has occurred.

Figure 32:
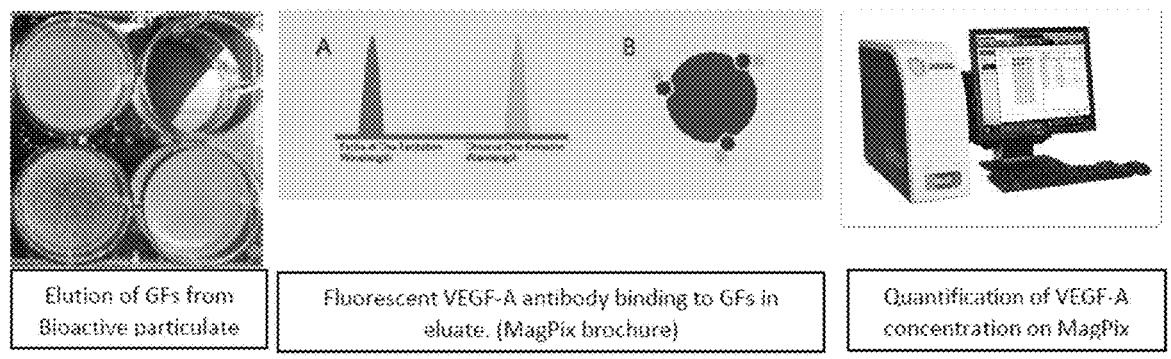
FIG. 32 is a set of pictures showing elution of GFs from Bioactive particulate, fluorescent VEGF-A antibody binding to GFs in eluate. (MagPix brochure) and quantification of VEGF-A concentration on MagPix.

FIG. 32 is a set of pictures showing elution of GFs from Bioactive particulate, fluorescent VEGF-A antibody binding to GFs in eluate. (MagPix brochure) and quantification of VEGF-A concentration on MagPix.

Figure 33:
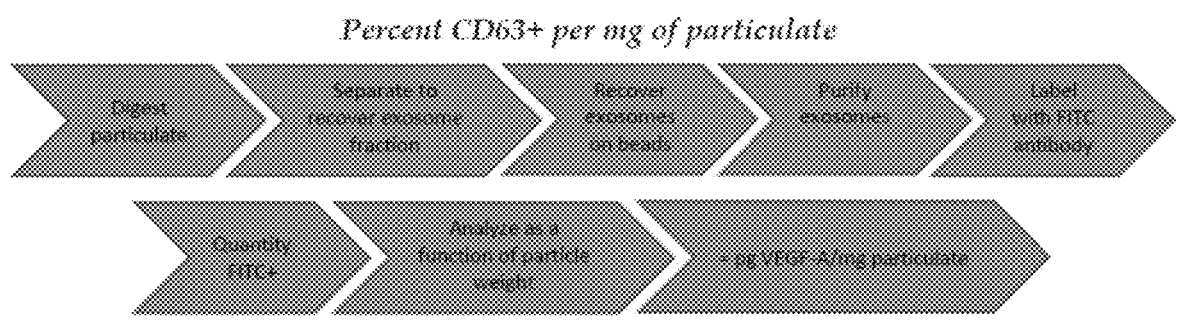
FIG. 33 is a representation of percent CD63+ per mg of particulate.

FIG. 33 is a representation of percent CD63+ per mg of particulate.

Figure 34:
FIG. 34 is a set of photographs showing fluorescent microscopy.

FIG. 34 is a set of photographs showing fluorescent microscopy for DAPI, PI and CD63 all at 10× magnification.

Figure 35:
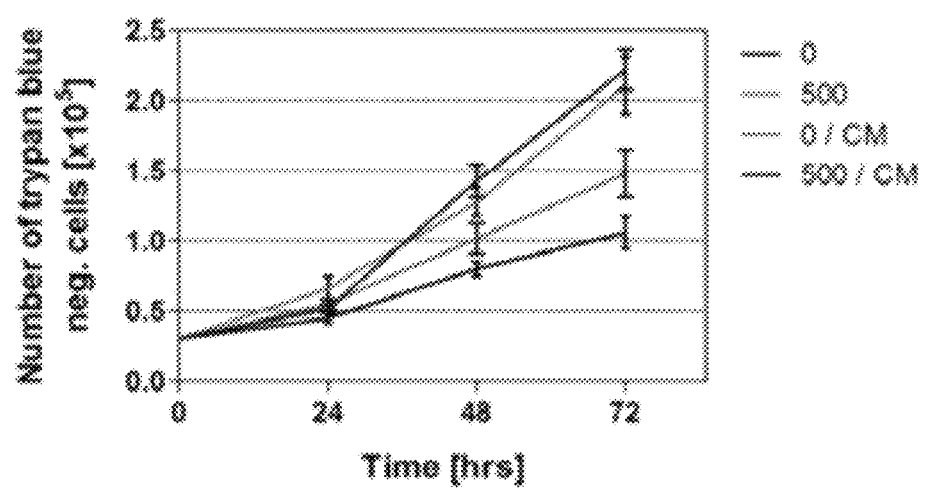
FIG. 35 is a table depicting the effect of Shockwave-conditioned media on cell count. Hochstrasser, 2016

FIG. 35 is a table depicting the effect of Shockwave-conditioned media on cell count. From Hochstrasser, 2016

Figure 36:
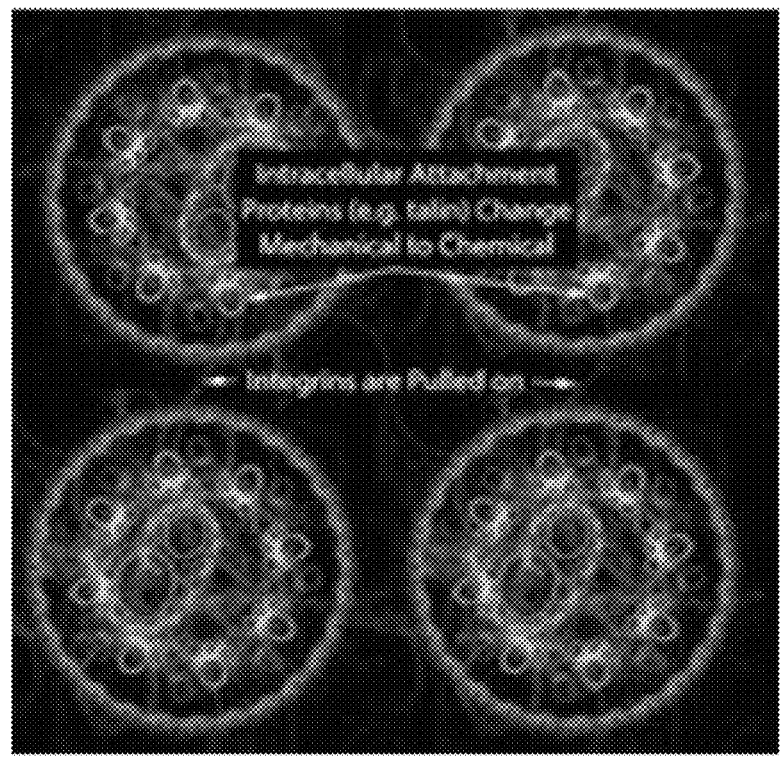

FIG. 36 is a depiction of intracellular attachment proteins, talin, change mechanical to chemical, integrins are pulled on from http://www.shockwavetherapy.education/index.php/theory/biological-effects.

Figure 37:
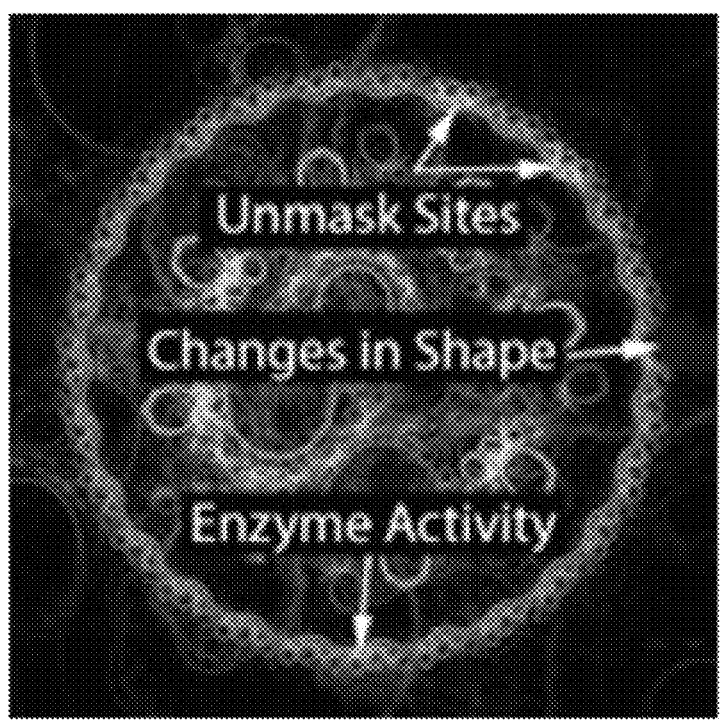
FIG. 37 is a depiction of unmask sites, changes in shape and enzyme activity.

FIG. 37 is a depiction of unmask sites, changes in shape and enzyme activity from http://www.shockwavetherapy.education/index.php/theory/biological-effects.

Figure 38:
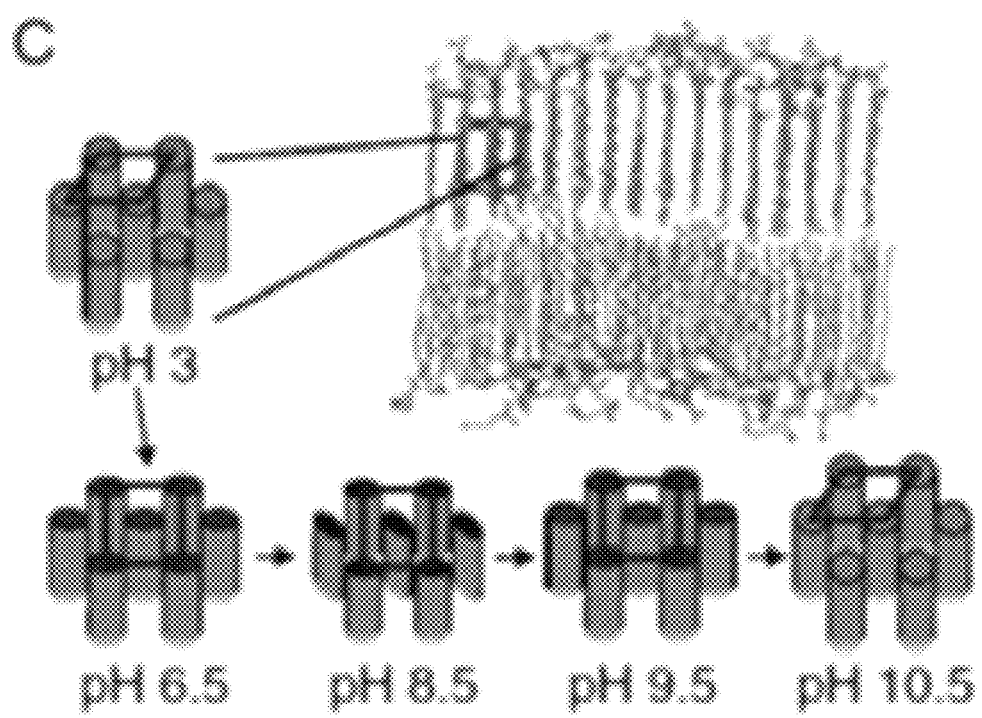
FIG. 38 is a depiction of a change in pH.

FIG. 38 is a depiction of a change in pH from https://www.sciencedaily.com/releases/2013/10/131001124012.htm.

With reference to the present invention which is a tissue regenerative biological composition which can be made from bone marrow, it is believed best understood by the exemplary methods used to process and recover the biological composition, as described below.

The first steps are to collect, recover and process bone marrow from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (1 g/L), Sodium Pyruvate; without L-glutamine, or HEPES. This cold media is used for packaging the spine segments for later processing. At this point the spine segment includes a plurality of vertebral bodies. The clinical technician must remove as much soft tissue as possible and cut each vertebral body with a saw. These vertebral bodies, once cleaned, of all adherent soft tissue around the cortical surfaces is removed.

Once a cleaned vertebral body is obtained, the next step involves cutting each vertebral body into pieces, each piece 204 roughly 1 cm$^3$. The cut pieces being immersed in a packing media. The exemplary packing media can be DMEM with 0.5 ml Heparin and 1.25 ml of DNAse added.

Once all the vertebral bodies have been cut, the pieces are taken to the bone grinder. The bone is ground into 4-10 mm pieces using packing media to help the pieces go through the grinder. The ground bone (bulk cortical-cancellous crushed) and all of the packing media, estimated volume of 500 ml are transferred into a jar where 0.5-1.0 ml of Gentamicin is added to the jar with ground bone and packing media. At this point, the crushed bone, including cellular soft marrow, is intermixed.

The step of mechanically separating these cellular components of bone marrow from the cadaverous bone is next performed. Transferring the bulk cortical-cancellous bone chips into a new jar with a CBT-Mixer in the jar. The bulk cortical-cancellous bone chips will go through four cycles as summarized in the table below. Each cycle, after cycle 1, contains three steps using a bone tumbler and sieve set. The sieve set has screens of various sizes, for example 500 μm and 180 μm.

| Step | Cycle 1 | Cycle 2 | Cycle 3 | Cycle 4 |
| --- | --- | --- | --- | --- |
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-μm and the bottom pan sieve. Discard decanted fluid. | Use the 500-μm, 180-μm and bottom pan sieve. Collect decanted fluid. | Use the 500-μm, 180-μm and bottom pan sieve. Collect decanted fluid. | Use the 500-μm, 180-μm and bottom pan sieve. Collect decanted fluid. |
| Centrifuge | N/A | Use decanted fluid. | Use decanted fluid. | Use decanted fluid. |

In cycle 1, the decanted fluid is discarded. To best understand this, conical tubes with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This is only to illustrate the effects of multiple tumbles 1-4 and the value in discarding the decanted liquid after the first tumble 1.

After each subsequent sieving of the bulk bone material, the decanted fluid containing the mixture with whole cells is collected and put into a collection jar. When the next three cycles are complete and the decanted fluid is all placed in the collection jar comingling the fluids to form a decanted fluid. Then the centrifugation of the combined decanted fluid occurs by placing the fluid in a number of 250 ml conical tubes using a 100 ml pipette. The centrifuge is programmed to 280×g for 10 minutes at room temperature, preferably about 20 degrees C. The fluid is passed through a blood filter to further remove any bone or spicules or clumps from the suspended cells. This completes the step of centrifuging and filtering. At this point, the mixture including whole cells has been separated from the soft marrow tissue and the remaining cancellous and cortical bone is discarded.

After this, the step of separating the cells from the non-whole cellular components by a density centrifugation occurs. The whole cells are in the interface and the non-whole cell components are in the supernatant above the interface. The mixture including is placed in 50 ml conical tubes with Ficoll and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid above the interface is removed include the desired non-whole cell components which exclude the whole cells.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 μm filters. Exosomes are further collected and separated within the suspension in multiple centrifugation steps with increasing centrifugal strength to sequentially pellet cells (300 g), microvesicles (10,000 g) and ultimately exosomes (100,000 g). Cells are deliberately removed to achieve the non-whole cell fragments and microvesicles.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions, such as ExoQuick™ and Total Exosome Isolation™ (TEI), that have been commercialized reduce the need for expensive equipment or technical know-how. Although their mode-of-action has not been disclosed or validated, these kits are commonly used.

Once the mixture is completed, the method can include additional steps. This leads to the use of a bone blend, preferably from the same vertebral bone or at least bone from the same donor.

When the mixture is prepared, it can have whole cells or even no whole cells, but will have the mechanically selected non-whole cellular components including vesicular components and active and inactive components of biological activity, cell fragments, cellular excretions, cellular derivatives, and extracellular components.

In one embodiment, the composition includes the whole cells in the mixture. In that embodiment, it is possible to provide bone particles with the mixture either in the mixture or separately to be combined at the time of use.

In one embodiment, the bone is ground to a particle size of 100-300 μm. The bone mixture has 1.5 cc of mineralized cancellous bone, 1.5 cc of mineralized cortical bone and 2.0 cc of demineralized cortical bone yielding 30 percent, 30 percent and 40 percent respectively of the total 5 cc (5 gram) of bone material. The ranges coincide with the 1 cc of mixture when resuspended in 3 cc of saline to provide a bone particle and mixture for implantation, which can be by packing, injection, scaffolding or any other suitable means, into a patient in a fracture healing procedure, by way of example.

Other ranges of bone particle sized and mixture can be employed depending on the application which, in this example, was bone regeneration. Lower volumes and concentrations may be more suited for less intrusive bone repairs or more if larger if larger amounts of material are needed as in a hip defect or repair.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making a biological composition, comprising:
    (a) grinding a cut vertebral body from a human cadaver donor to produce a mixture comprising crushed vertebral bone and bone marrow;
    (b) mechanically separating cellular and non-cellular components of the bone marrow from the vertebral bone in the mixture by tumbling and sieving the vertebral bone from a decanted fluid of the bone marrow comprising cellular components comprising whole cells, and non-whole cellular components comprising non-whole cell components;
    (c) concentrating the decanted fluid by centrifugation;
    (d) filtering the decanted fluid through a blood filter to form a mixture including the cellular and non-whole cellular components and remove any remaining vertebral bone;
    (e) separating the cellular components and non-whole cellular components of the bone marrow directly from the mixture of step (d) by density gradient centrifugation, wherein the separation by centrifugation establishes a cell density gradient;
(f) collecting non-cellular fractions, non-cellular components, or combinations thereof of predetermined density from the gradient;
(g) washing the non-cellular fractions, non-cellular components, or combinations thereof to create a mixture;
(h) suspending the mixture of step (g) to a predetermined concentration in a polyampholyte cryoprotectant to form a coated biological composition;
(i) freezing the coated biological composition at a predetermined controlled rate; and
(j) packaging a bone blend having particles of 100 to 300 μm of demineralized cortical bone, mineralized cortical bone, and mineralized cancellous bone with the coated biological composition.

2. The method of claim 1, wherein the coated biological composition is frozen in step (i) before packaging separately with the bone blend in step (j), and wherein the method further comprises:
(k) thawing the frozen coated biological composition;
(l) diluting the thawed coated biological composition in saline;
(m) mixing the coated biological composition with the bone blend; and
(n) implanting the diluted coated biological composition and the bone blend by packing, injection, or any other suitable means into a patient.

3. The method of claim 2, wherein the step of thawing the frozen coated biological composition occurs at a temperature of 37 degrees C. for 2 to 3 minutes.

4. The method of claim 2, wherein the thawed coated biological composition mixed with the bone blend is re-frozen after step (m) for storage prior to step (n).

5. The method of claim 2, wherein the thawed coated biological composition mixed with the bone blend is refrigerated after step (m) for storage prior to step (n).

6. The method of claim 2, wherein the thawed coated composition mixed with the bone blend is stored at room temperature after step (m) for storage prior to step (n).

7. The method of claim 1, wherein the bone blend is intermixed with the coated biological composition prior to freezing in step (i).

8. The method of claim 7, further comprising:
(k) thawing the frozen coated biological composition intermixed with the bone blend;
(l) diluting the thawed coated biological composition intermixed with the bone blend in saline; and
(m) implanting the diluted coated biological composition intermixed with the bone blend by packing, injection, or any other suitable means into a patient.

9. The method of claim 8, wherein the step of thawing the frozen coated biological composition intermixed with the bone blend occurs at a temperature of 37 degrees C. for 2 to 3 minutes.

10. The method of claim 8, wherein the thawed coated biological composition intermixed with the bone blend is re-frozen after step (l) for storage prior to step (m).

11. The method of claim 8, wherein the thawed coated biological composition intermixed with the bone blend is refrigerated after step (l) for storage prior to step (m).

12. The method of claim 8, wherein the thawed coated composition intermixed with the bone blend is stored at room temperature after step (l) for storage prior to step (m).

* * * * *